United States Patent
Ecker et al.

(10) Patent No.: US 6,558,633 B1
(45) Date of Patent: May 6, 2003

(54) CHEMICAL REACTION APPARATUS AND METHODS

(75) Inventors: David J. Ecker, Leucadia, CA (US); Oscar Acevedo, San Diego, CA (US); Normand Hebert, Cardiff, CA (US); Peter W. Davis, Carlsbad, CA (US); Jacqueline R. Wyatt, Carlsbad, CA (US); John S. Kiely, San Diego, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/309,925

(22) Filed: Sep. 21, 1994

(51) Int. Cl.$^7$ .............................. C12M 1/18; B01L 9/00
(52) U.S. Cl. ...................... 422/134; 422/50; 422/131; 435/288.5; 435/288.4; 435/305.2
(58) Field of Search ................................. 422/131, 134; 435/300, 301, 310, 288.4, 288.5, 305.2; 935/88; 525/54.11

(56) References Cited

U.S. PATENT DOCUMENTS

| | | | |
|---|---|---|---|
| 3,531,258 A | 9/1970 | Merrifield et al. ............ | 23/252 |
| 4,353,989 A | 10/1982 | Bender et al. .............. | 435/287 |
| 4,362,699 A | 12/1982 | Verlander et al. ........... | 422/131 |
| 4,415,732 A | 11/1983 | Caruthers .................... | 536/27 |
| 4,458,066 A | 7/1984 | Caruthers .................... | 536/27 |

(List continued on next page.)

FOREIGN PATENT DOCUMENTS

| | | |
|---|---|---|
| EP | 0138075 | 9/1984 |
| WO | WO 89/10977 | 11/1989 |
| WO | WO 90/00626 | 1/1990 |
| WO | WO 90/03382 | 4/1990 |
| WO | WO 91/16457 | 10/1991 |
| WO | WO 92/00091 | 1/1992 |
| WO | WO 92/10588 | 6/1992 |
| WO | WO 92/20702 | 11/1992 |
| WO | WO 93/17126 | 9/1993 |
| WO | WO 93/22678 | 11/1993 |
| WO | WO 94/05394 | 3/1994 |
| WO | WO 94/17412 | 8/1994 |
| WO | WO 94/18226 | 8/1994 |
| WO | WO 95/25116 | 9/1995 |

OTHER PUBLICATIONS

The MultiScreen Assay System Millipore Advertisement *Science* Sep. 9, 1994 vol. 265.

Human Genome 1991–92 Program Report U.S. Department of Energy Jun. 1992 "Sequencing by Hybridization: Methods to Generate Large Arrays of Oligonucleotides".

Glass Fiber Filter Plates *Science* Jun. 17, 1994 264:1791.

Daniels, et. al, Poster #T81 at the Protein Society meeting, San Diego, CA, 1989.

Fitzpatrick, et. al., presented in a paper entitled "Membrane Supports for DNA Synthesis", at the 1993 "Innovations and Perspectives in Solid–Phase Synthesis" conference at the University of Oxford.

Merrifield B. Solid Phase Synthesis *Science* 1986 232:341–347.

Merrifield B. Solid Phase Peptide Synthesis I. The Synthesis of a Tetrapeptide *J. Am. Chem. Soc.* 1963 85:2149–2154.

(List continued on next page.)

*Primary Examiner*—Glenn Caldarola
(74) *Attorney, Agent, or Firm*—Woodcock Washburn LLP

(57) ABSTRACT

Chemical reaction apparatus, materials and methods are provided for the automatable, efficient synthesis of chemical species and libraries. In accordance with preferred embodiments, chemical droplet generation and direction techniques are employed to prepare oligomers and libraries of chemical species. Reaction assemblies adapted for efficient synthetic employment and for improved collection are also disclosed.

2 Claims, 5 Drawing Sheets

U.S. PATENT DOCUMENTS

| | | | |
|---|---|---|---|
| 4,483,964 A | 11/1984 | Urdea et al. | 525/54.11 |
| 4,500,707 A | 2/1985 | Caruthers | 536/27 |
| 4,517,338 A | 5/1985 | Urdea et al. | 525/54.11 |
| 4,562,157 A | 12/1985 | Lowe et al. | 435/291 |
| 4,598,049 A | 7/1986 | Zelinka et al. | 435/287 |
| 4,668,476 A | 5/1987 | Bridgham et al. | 422/62 |
| 4,668,777 A | 5/1987 | Caruthers | 536/27 |
| 4,671,941 A | 6/1987 | Niina et al. | 422/131 |
| 4,701,304 A | 10/1987 | Horn et al. | 422/62 |
| 4,725,677 A | 2/1988 | Koster | 536/27 |
| 4,728,502 A | 3/1988 | Hamil | 422/116 |
| 4,746,490 A | 5/1988 | Saneii | 422/62 |
| 4,748,002 A | 5/1988 | Neimark et al. | 422/116 |
| 4,816,513 A | 3/1989 | Bridgham et al. | 525/54.11 |
| 4,861,866 A | 8/1989 | Durrum et al. | 530/333 |
| 4,866,166 A | 9/1989 | Wigler | 536/27 |
| 4,882,127 A | 11/1989 | Rosenthal et al. | 422/50 |
| 4,923,901 A | 5/1990 | Koester | 521/53 |
| 4,973,679 A | 11/1990 | Caruthers | 536/27 |
| 5,019,348 A | 5/1991 | Ohms et al. | 422/63 |
| 5,073,495 A | 12/1991 | Anderson | 435/284 |
| 5,106,585 A | 4/1992 | Minami et al. | 422/68.1 |
| 5,112,575 A | 5/1992 | Whitehouse et al. | 422/116 |
| 5,112,736 A * | 5/1992 | Caldwell et al. | 935/88 |
| 5,132,418 A | 7/1992 | Caruthers | 536/27 |
| RE34,069 E | 9/1992 | Koster | 536/27 |
| 5,143,854 A | 9/1992 | Pirrung et al. | 436/518 |
| 5,174,962 A | 12/1992 | Brennan | 422/78 |
| 5,175,209 A | 12/1992 | Beattie et al. | 525/54.11 |
| 5,182,366 A | 1/1993 | Huebner et al. | 530/334 |
| 5,198,368 A * | 3/1993 | Khall et al. | 436/178 |
| 5,202,418 A | 4/1993 | Lebl et al. | 530/334 |
| 5,210,264 A | 5/1993 | Yau | 558/167 |
| 5,221,518 A | 6/1993 | Mills | 422/62 |
| 5,240,680 A | 8/1993 | Zuckermann et al. | 422/67 |
| 5,243,540 A | 9/1993 | Van Albert et al. | 364/500 |
| 5,252,296 A | 10/1993 | Zuckermann et al. | 422/116 |
| 5,288,464 A | 2/1994 | Nokihara | 422/101 |
| 5,288,468 A | 2/1994 | Church et al. | 422/116 |
| 5,324,483 A * | 6/1994 | Cody et al. | 422/131 |
| 5,338,831 A | 8/1994 | Lebl et al. | 530/334 |
| 5,342,585 A | 8/1994 | Lebl et al. | 422/131 |
| 5,356,596 A | 10/1994 | Nokihara et al. | 422/131 |
| 5,362,447 A | 11/1994 | Nokihara | 422/131 |
| 5,368,823 A | 11/1994 | McGraw et al. | 422/134 |
| 5,449,754 A | 9/1995 | Nishioka | 530/334 |

OTHER PUBLICATIONS

Stewart and Young, "Solid Phase Peptide Synthesis", 2nd Ed., Pierce Chemical Company, Illinois, 1984, pp. 88.

M. Blackburn and M. Gait, *Nucleic Acids in Chemistry and Biology* Eds., IRL Press 1990 112–130.

Alul, et al., Oxalyl–CPG: a labile support for synthesis of sensivitive oligonucleotide derivatives *Nucleic Acids Research* 1991 19:1532–1527.

Wright et al. Large Scale Synthesis of Oligonucleotides via Phosphoramidite Nucleosides and a High–loaded Polystyrene Support *Tetrahedron Letters* 1993 34:3373.

Beaucage et al. Advances in the Synthesis of Oligonucleotides by the Phosphoramidite Approach *Tetrahedron* 1992 48:2223.

Berner et al. Studies on the role of tetrazole in the activation of phosphoramidite *Nucleic Acids Research* 1989 17:853.

Dahl et al. Mechanistic studies on the phosphoramidite coupling reaction in oligonucleotide synthesis *Nucleic Acids Research* 1987 15:1729.

Nielson et al. Thermal Instability of Some Alkyl Phosphorodiamidites *J. Chem. Research* 1986 26–27.

Sekine et al. Synthesis and Properties of S,S–Diaryl Nucleoside Phosphorodithioates in Oligonucleotide Synthesis *J. Org. Chem.* 1979 44:2325–2326.

Dahl, O., Preparation of Nucleoside Phosphorothioates, Phosphorodithioates and Related Compounds *Sulfur Reports* 1991 11:167–192.

Kresse J. et al. The use of S–2–cyanoethyl phosphorothioate in the preparation of oligo 5'–deoxy–5'thiothymidylates *Nucleic Acids Research* 1975 2:1–9.

Eckstein F. Nucleoside Phosphorothioates *Ann. Rev. Biochem.* 1985 54:367–402.

Lipshutz R. Likelihood DNA Sequencing by Hydridization *Journal of Biomolecular Structure & Dynamics* 1993 11:637–653.

Southern et al. Analyzing and Comparing Nucleic Acid Sequences by Hybridization to Arrays of Oligonucleotides: Evaluation Using Experimental Models *Genomics* 1992 13:1008–1017.

* cited by examiner

CHEMICAL REACTION APPARATUS AND METHODS

FIELD OF THE INVENTION

This invention is concerned with novel apparatus, materials and methodologies for synthesizing chemical compounds, especially oligomers. Chemical reactions are accomplished on surfaces in a fashion which is both easy and economical and which is amenable to the attainment of high yields. Automation of chemical reaction processes is facilitated in the present invention. Synthesis of oligomers, especially oligonucleotides and polypeptides, is especially benefitted by the employment of the present invention. A wide variety of other chemical reactions can be achieved in accordance with the present invention, however. The present invention is also suited for the preparation of chemical libraries which are useful per se, inter alia for screening purposes and otherwise.

BACKGROUND OF THE INVENTION

It has been proposed heretofore to employ apparatus commonly called an "ink jet" for the delivery of deblocking reagents in solid state oligomeric reactions. Such proposal, however, is crude, is limited in scope, and generally requires non-automatable procedures for its employment. Thus, it has been proposed to use an "ink jet" apparatus to place droplets of a deblocking reagent, zinc bromide, upon specified locations of a reaction surface to deblock a growing oligonucleotide chain to render it amenable to chain elongation. This has been proposed for use, for example, on a microscope slide. Following the delivery of deblocking reagent, it was proposed to manipulate the microscope slide such as by dipping it into a quantity of further reagent to accomplish a chain elongation. Further application of the "ink jet" delivery of chemical reagent was then proposed, however realignment of the microscope slide would be necessitated by that proposed methodology. In addition to the cumbersome nature of the prior proposal and its lack of suitability to full automation, only relatively small harvests of oligomeric product were anticipated using the proposed scheme.

There is a great need for chemical reaction apparatus, materials and attendant methodologies which permit the automated, high yield, relatively large scale synthesis of chemical species, especially oligomers. The apparatus and methodologies provided by the present invention now enable the use of chemical "jetting" technology for the practical synthesis of chemical and biochemical products in high yield and with ease of synthesis. There is also provided a need for synthetic systems which deliver complex synthesized products to receiving vessels with ease and in high yield.

The apparatus and methods of the present invention also address a long-felt need by permitting the preparation of libraries of chemical compounds having predictable diversity among the functional moieties thereupon.

This invention also diminishes waste stream pollution associate with many prior synthetic technologies through the precision application of reagent moieties in synthetic schemes.

Precisely arrayed pluralities of defined chemical compounds are also possible through employment of this invention. Binding, reaction, degradation, chemical and biological interaction and other testing protocols may, thus, be performed with unparalleled convenience through practice of embodiments of this invention.

The invention minimizes reagent usage such that the impact of toxic, explosive, radioactive, or expensive sensitive materials on syntheses is reduced.

SUMMARY OF THE INVENTION

In accordance with the present invention, there are provided chemical reaction apparatuses. These apparatuses comprise a reaction support having a first surface (alternatively called a reaction surface) thereupon. The reaction surface is considered to have a plurality of preselected reaction sites upon it. These are generally in a regular geometric array such as a grid, but may be in other patterns as well. The apparatus further comprises a first droplet generator for jetting reactant droplets upon the first surface. The apparatus further comprises a second droplet generator for jetting droplets of a second reactant species upon the first surface. The droplets of each of the first and second droplet generators are under control of a control means such as a general or special purpose digital computer, with attendant switches and actuators, for causing the droplets from each of the droplet generators to impact upon definable sets of the preselected reaction sites on the reaction surface of the reaction support. The impacting of the droplets upon the sets of reaction sites is preferably in accordance with a preselected pattern or patterns. In this way, chemical reactants can be directed to particular reaction sites upon the reaction surface in any desired order so as to achieve desired chemical reactions at such reaction site without the need for removing, manipulating, and redeploying the reaction support.

In accordance with preferred embodiments, three, four, or more droplet generators are provided, each connected to one or more chemical reactant reservoirs, in order to provide diversity among the chemical reactions possible at the reaction surface. The control means is preferably programmed to deliver different sequences of reactants at different reaction sites so as to synthesize differing chemical compounds at such sites. Preferably, the methods of the invention are performed iteratively such that relative complex molecules, such as oligomers, can be synthesized.

Synthesis has been found to be benefitted by employment of porous reaction supports, especially those having the capability of transporting fluid from the first (or reaction) surface to a second surface thereof. Improvement of yield through exploitation of the internal pore volume of the support and amenability for improved product harvest is also now possible.

Once the different chemical moieties have been synthesized at the plurality of reaction sites, they may be employed in a variety of highly useful ways. Thus, the different chemical moieties may be exposed to test solutions, such as bodily fluids of a test animal, to diagnose or ascertain bodily states in such animal. A wide variety of assays may thus be formulated using the apparatus and methodologies of the present invention. In accordance with other utilities, the chemical species thus formed may be used as probes in biological systems or as primers or substrates for polymerase chain reaction amplification or the like. Hybridization studies may also be conducted using apparatus and methods in accordance with the present invention, where the products of the methodologies are oligonucleotides, polypeptides or other hybridizable species. All of the foregoing utilities are known per se to those skilled in the art.

In accordance with other preferred embodiments of the invention, reaction apparatuses are provided where one or more droplet generators, each in fluid communication with pluralities of reactant reservoirs, are employed to perform synthesis. Control means are caused to effect the operation of valving moieties to select reactants in appropriate orders to achieve the desired reactions at individual reaction sites.

In accordance with the invention, methods for synthesizing chemical species comprise identifying a plurality of reaction sites upon a reaction surface and jetting upon a first set of such reaction sites, droplets of fluid comprising a first chemical reactant. The methods also comprise jetting upon a second set of such reaction sites, droplets of fluid comprising a second chemical reactant species. It will be appreciated that, through practice of the present invention, the first jetted reactant species and the second jetted reactant species may be jetted to the same or different reaction sites on the reaction surface Control means for effectuating the jetting of such fluids upon the selected sets of reaction sites is also invoked to attain the ends of the invention. Iterative jetting of reactant species permits the elaboration of wide varieties of chemical moieties as the reaction sites and permits the generation of libraries of diverse species.

It is also possible to employ the present invention in a hybrid fashion by combining it with other chemical reaction schemes. Thus, for example, a support for reaction may be coated with an initial reactant species and then reacted through the jetting of chemical reactants in preselected locations on the surface. Subsequent reaction at the selected locations on the surface in accordance with the invention may ensue whereby a plurality of reactant species are delivered to such locations. Thus, by pretreating the support where the reaction is to occur with a first reactant moiety, certain economies of scale may be attained. The employment of chemical jetting technology to deliver often expensive reagents for at least some of the subsequent steps, is, however, preferred.

At any reaction site, either or both of the first and second reactants may be delivered thereto. Thus, at the reaction site, either the first reactant, the second reactant, or the first reactant followed by the second reactant can be so delivered. The ensuing chemical reactions will depend upon the identity and order of chemical reactants delivered to any particular reactant site.

This is also true where an initial reaction species is applied to the support prior to the delivery of jetted reactants. In such case, at reaction site $R_n$, one of four situations will prevail after jetting of two reactants has occurred. First, it may be that neither the first nor the second reactant are directed to a given reaction site. In this case, only the initial reaction species will have been delivered to this site. In two additional cases, either the first reactant or the second reactant, but not both is jetted to site. In this case, two different combinations of two reagents are delivered to the site. Finally, it may be seen that both the first and the second reactant can be jetted to the site whereupon three reaction species will have been so delivered. Persons of ordinary skill in the art will readily appreciate how a complex series of reactants can be delivered to particular sites on a reaction surface to achieve complex and varied chemical reactions. The present invention is suited to the delivery of a large variety of chemical species including reagents, intermediates, blocking and deblocking agents, monomers, dimers, oligomers, solvents, washing agents, cleaving agents and the like.

In accordance with preferred embodiments, the methodologies of the present invention are performed iteratively. Thus, three, four, five, and more reactants can be delivered to a reaction surface in varying combinations at different reaction sites on the surface. The number of different chemical moieties which may, thus, be elaborated is extraordinarily numerous and varied. It is, thus, possible to generate, isolate and recover a wide variety of different chemical species in a highly automated fashion on small reaction surfaces. The present invention also provides reaction assemblies wherein a reaction support surmounts a collection plate, preferably one having a plurality of collection wells. Transport of chemical species through the reaction support enables their collection in the collection wells where they may be easily recovered, analyzed, tested, hybridized, screened, assayed and otherwise utilized. The efficient deposition of product species into such collection vessels is a particularly advantageous aspect of the invention.

BRIEF DESCRIPTION OF THE DRAWINGS

FIG. 8A shows reaction wells in a shaped body while

DESCRIPTION OF PREFERRED EMBODIMENTS

The present invention provides significant improvements in chemical synthesis and recovery technology. The apparatuses and methods of the present invention are advantageously employed in the preparation of oligomers, especially oligonucleotides and polypeptides, and in the preparation of libraries of compositions having diverse chemical structure. They are also useful for the synthesis of a wide variety of non-oligomeric molecules, especially those requiring hazardous or expensive materials. In accordance with the present invention, it has now been found to be highly desirable to effect chemical reactions upon a reaction support through the sequential jetting of chemical reagent species upon predefined sets of reaction sites on such surfaces. The problems associated with mounting and dismounting of reaction surfaces from the chemical jetting apparatus is avoided or minimized through employment of embodiments of the present invention.

Figure 1:
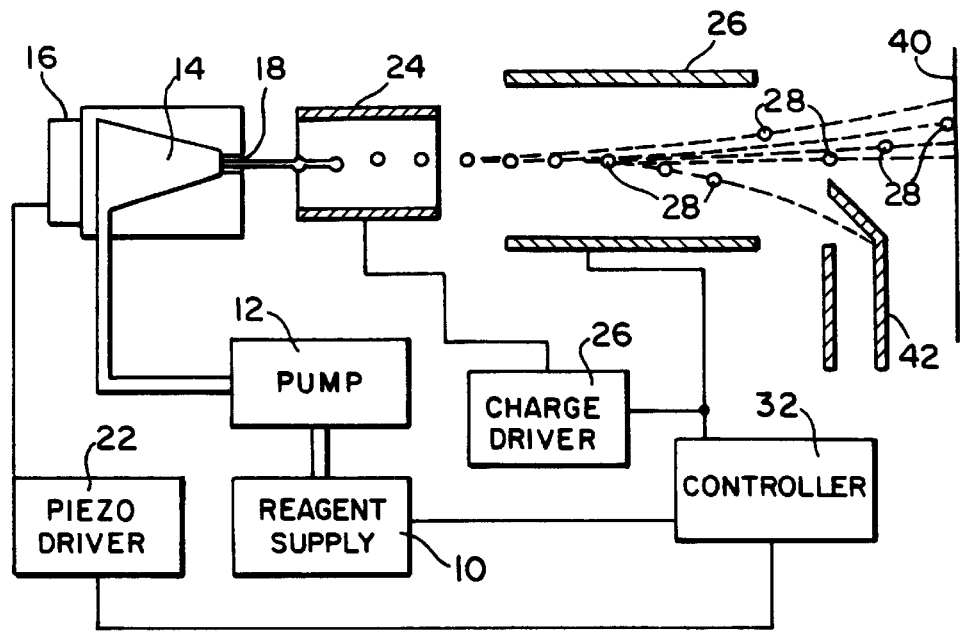
FIGS. 1 and 2 are generalized drawings of droplet generating apparatus useful in the invention depicting salient features.

FIG. 1 is a depiction of a chemical jetting apparatus which may be used with embodiments of the present invention. It will be appreciated that chemical jetting apparatus suitable for use in the present invention may be viewed as being essentially similar to apparatus used in "ink jet" printing. Ink jet printers are known per se and have achieved a separate status in the patent and other literature. For example, class 346 of the patent classification of the United States Patent and Trademark Office contains a large number of patents directed to ink jet technology, to methodologies for employment of ink jets, and to apparatus for use therein. All may be useful in the practice of this invention. While certain modifications of basic ink jets are preferred for use in accordance with the present invention—chiefly to render the same inert with respect to the chemical reactants employed—the basic mechanical and materials considerations which attend the provision of ink jet apparatus apply to the manufacture of chemical jetting apparatus as well.

Referring now to FIG. 1, chemical jetting devices are conventionally actuated through piezoelectric devices. A source of chemical reagent, 10 is provided, conventionally through a pumping means, 12 to a chamber, 14 in mechanical communication with a piezoelectric material, 16. The chamber 14, is provided with one or more orifices, 18 through which droplets of reagent, 28 may be expressed through the controlled pumping action of the piezoelectric material. The piezoelectric device is controlled by a driver, 26 which, in turn, is controlled by controller, 32. In some apparatuses, droplets, 28 are provided with an electric charge in a chamber, 24 upon their emergence from the orifice and are accelerated in one or more planes in an acceleration chamber, 26 under the influence of an applied voltage controlled by the controller, 32. It will be appreciated that the overall effect of the foregoing arrangement is to provide a series of droplets at spaced intervals traveling in predetermined vectors, as showing established by the controller in response to operator programming. It is well known to direct individual droplets of liquid, 28 to various selected locations on a reaction surface, 40 which, in embodiments of the present invention, is a reaction surface whereupon chemical reactions take place. Droplets, which are not to be directed to particular locations on the surface are, in accordance with this embodiment, directed to a "gutter", 42 for environmentally approved disposal or recycling.

The foregoing method of providing droplets and directing the same to particular locations on a reaction surface, with excess droplets being diverted to a gutter is known as a "continuous jet" type of device. It will be appreciated that the elements of reagent supply, pump, piezoelectric device chambers, orifices, electrodes, and the like—in short, those elements which are required to produce droplets of chemical reagent and to direct them in preselected directions—are conventionally and are conveniently denominated a "jetting head" or, preferably, a "droplet generator." These two terms are used interchangeably in the present application. While droplet generators may not conventionally be considered to include chemical reservoirs, plumbing, controllers, connectors and the like, it will be understood that all such apparatus as may be required to effectuate the delivery of reagent droplets in accordance with the present invention are included as needed and will not necessarily be separately recited hereinafter.

Figure 2:
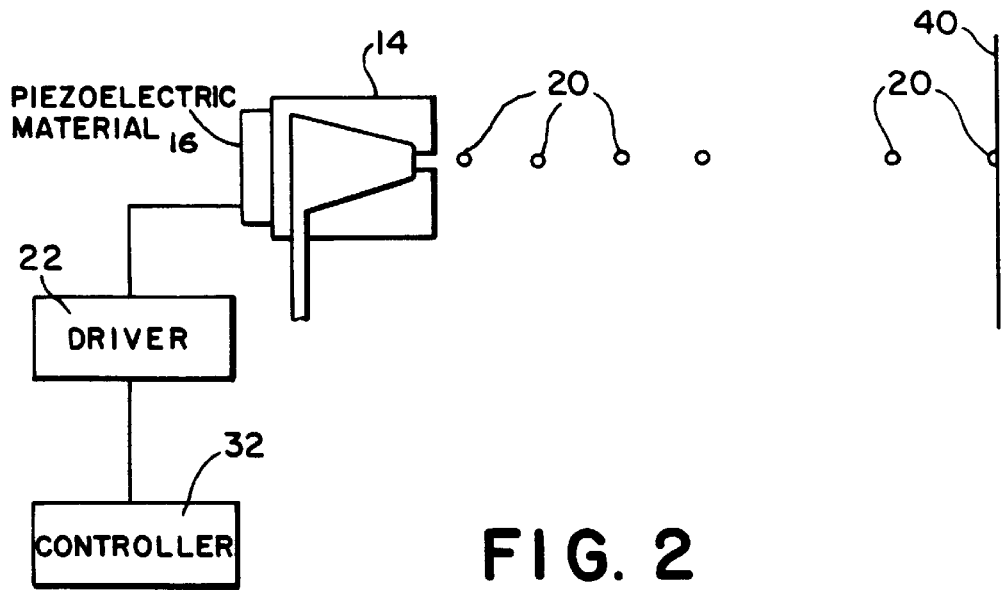

Another form of chemical jetting is conventionally denominated a "droplet on demand" device. Such a device is depicted in FIG. 2. It will be appreciated that rather than have a uniform stream of chemical reagent droplets provided by the apparatus, unneeded droplets being directed to a gutter, in droplet on demand systems, droplets are provided only when actually required for distribution to the reaction surface, 40. While it is convenient to use electrostatic directing means under control of a controller to direct these drops, it is also possible, and in many cases preferred, to physically move the source of the droplets—the droplet generator—with respect to the reaction surface or, vice versa, the reaction surface with respect to the source of the droplets, thus to deliver droplets to particular locations on the reaction surface in an imagewise, preselected fashion. Indeed, combinations of both directing techniques may also be employed. In some embodiments, it is possible to rely upon the impetus provided by the piezoelectric material, 16 upon the reagent, forcing the same through the orifice with sufficient kinetic energy to impact the reaction surface without additional acceleration. In any event, the piezoelectric driver, 22 and whatever motion of the droplet generator or reaction surface 40, may be required is under control of a controller, 32.

Irrespective of which form of chemical reagent droplet generator is selected, it will be appreciated that droplets of chemical reagent will be provided at a reaction surface in a fashion which is preselected as to location. Thus, the reagents may be applied in an imagewise fashion to specific sites on the reaction surface. In accordance with certain preferred embodiments of this invention, reagents are applied at sets of such sites such as in an array defined upon the reaction surface. Thus, a matrix of sites is conveniently defined upon the reaction surface and one or more reagents jetted to sets or subsets of such sites in amounts and in orders of deposition consistent with the chemical synthesis desired at each site. Any of the chemical jetting apparatus described above may be used for jetting the reagents to these sites and, indeed, any of the apparatus, methods, and materials which have been known heretofore for use in conjunction with ink jet printing, which are capable of jetting liquids to predefined locations on a surface, may also be used or easily modified for use in accordance with the present invention to deposit reagents at preselected sites upon a reaction surface. It will thus be appreciated that the present invention is not limited to any particular droplet generator or control means so long as the droplet generator and associated control means are effective for delivering the reagent to preselected locations on the reaction surface.

It is preferred to provide the chemical jetting head in materials that are inert with respect to the chemical reagents being delivered. Thus, it is preferred that the apparatus be constructed of materials such as glass, ceramic, porcelain, inert plastic, inert or passivated metal, and other material which is consisted with the reagent to be jetted by the particular jetting head and associated equipment. Persons of ordinary skill in the art will have no difficulty in determining appropriate materials for the construction of apparatus useful for the practice of the present invention upon consideration of the chemical and/or corrosive nature of the chemical reagents to be dispensed by the apparatus. It is convenient to employ polytetrafluoroethylene (PTFE) and other relatively inert polymers for the storage, transmission, and jetting of chemical reagents in accordance with this invention. Stainless steel is another preferred material, especially for the jetting head itself, while glass finds great utility for the storage of chemical reagents.

It will be appreciated that many piezoelectric materials are relatively chemically inert. Accordingly, selection of an appropriate piezoelectric material for inclusion in the chemical jetting apparatuses of this invention will be a matter of routine as well. Polyvinylidine fluoride (PVDF) is one piezoelectric material which is relatively inert to most chemical species and may be used in the practice of this invention. Certain other piezoelectric materials are metallic and are inert with respect to many reagent and may, accordingly, also be used. All such materials are contemplated hereby.

Prior attempts to employ droplet delivery for synthesis of chemical species at a reaction surface have employed single chemical delivery heads delivering a single reagent adapted for the deprotection of chemical moieties found on the reaction surface. It will be appreciated that this is a highly inefficient technique and one in which the attainment of high density of chemical synthesis on the reaction surface cannot easily be achieved. This is so, inter alia, because the reaction surface must generally be submitted to other chemical treatments with reagents other than those provided by the droplet delivery device. It is generally necessary to dismount the reaction surface from the droplet delivery apparatus for these further chemical treatments. Realignment is difficult and time consuming, thus efficiency is lost.

Figure 3:
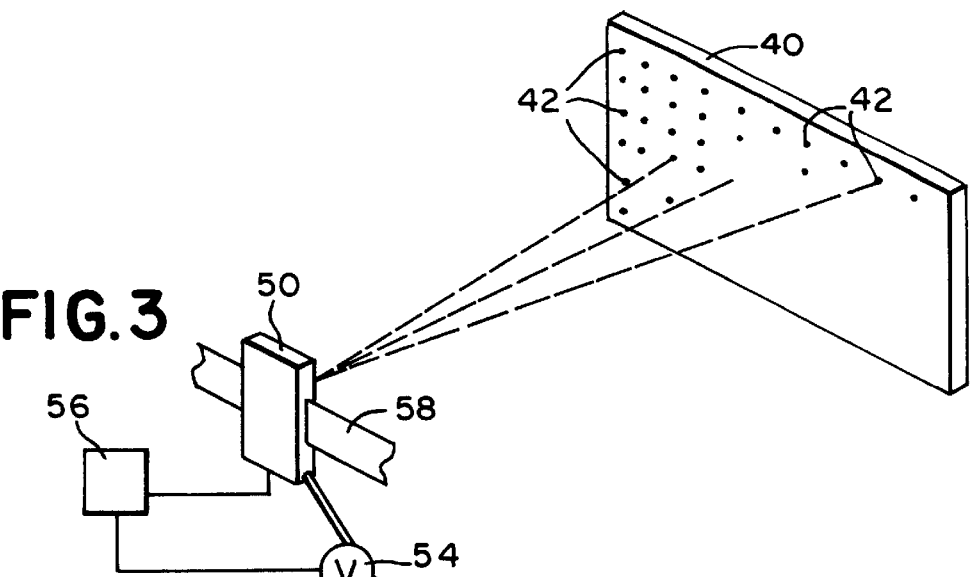
FIG. 3 depicts a single head droplet generating apparatus, in schematic, wherein a plurality of reagent reservoirs is in fluid communication with the droplet generating head. Delivery of chemical species to a reaction surface having a plurality of reaction sites is depicted.

FIG. 3 is directed to apparatus which provides great efficacy in the synthesis of chemical species on reaction surfaces. A droplet generating head, 50, which may be of the continuous droplet, droplet on demand, or other form, is provided in fluid communication with a plurality of chemical reagent reservoirs, 52. Valving means, 54 is also provided and this means is preferably electromechanical actuatable under control of a controller, 56. In accordance with preferred embodiments, the chemical droplet generating head, 50 is traversable in one or more directions through electromechanical means as is known for use in connection with ink jet printing heads. Such traversing means, 58, which is optional but preferred, permits the deposition of droplets of reagent at reactions sites, 42 on reaction surface, 40. Traversing through x or xy planes may be performed as convenient.

As will be appreciated, use of the present invention will permit the automation of chemical syntheses since the delivery of reagents in a sequential fashion to any particular reaction site on a reaction surface can be controlled through controllers such as general purpose digital computers or special purpose digital computers or processors. While it is not essential that the steps of the reaction sequence be controlled electromechanically by control means, this is generally preferred. Thus, while the valving means traversing means, etc, 54 can be actuated manually and still fall within the spirit of the present invention, it is greatly preferred that control means e.g. a computer, actuate the valves electromechanically and traverse the droplet generator in accordance with programmed demands for particular reagents. A wide variety of reagent storage, valving, plumbing and other ancillary apparatus may be employed within the spirit of this invention so long as the same are generally inert with respect to the reagents in contact with them. Similarly, the apparatus may be encased in a special atmosphere, may be operated with exclusion of light or moisture, and may be oriented in any convenient direction as may be preferred for any particular synthesis. All such modifications are contemplated hereby.

It will be appreciated that it may be necessary to rinse or otherwise purge the chemical jet reaction system when different chemical reagents are selected for use. Thus, it is preferred to provide appropriate solvent means effective to remove one reagent from the system prior to the provision of a second reagent thereto. Persons of ordinary skill in the art will have no difficulty selecting appropriate solvent means and washing steps to effect this goal. Unwanted materials may be jetted to a dump or gutter for recycling or disposal.

Figure 4:
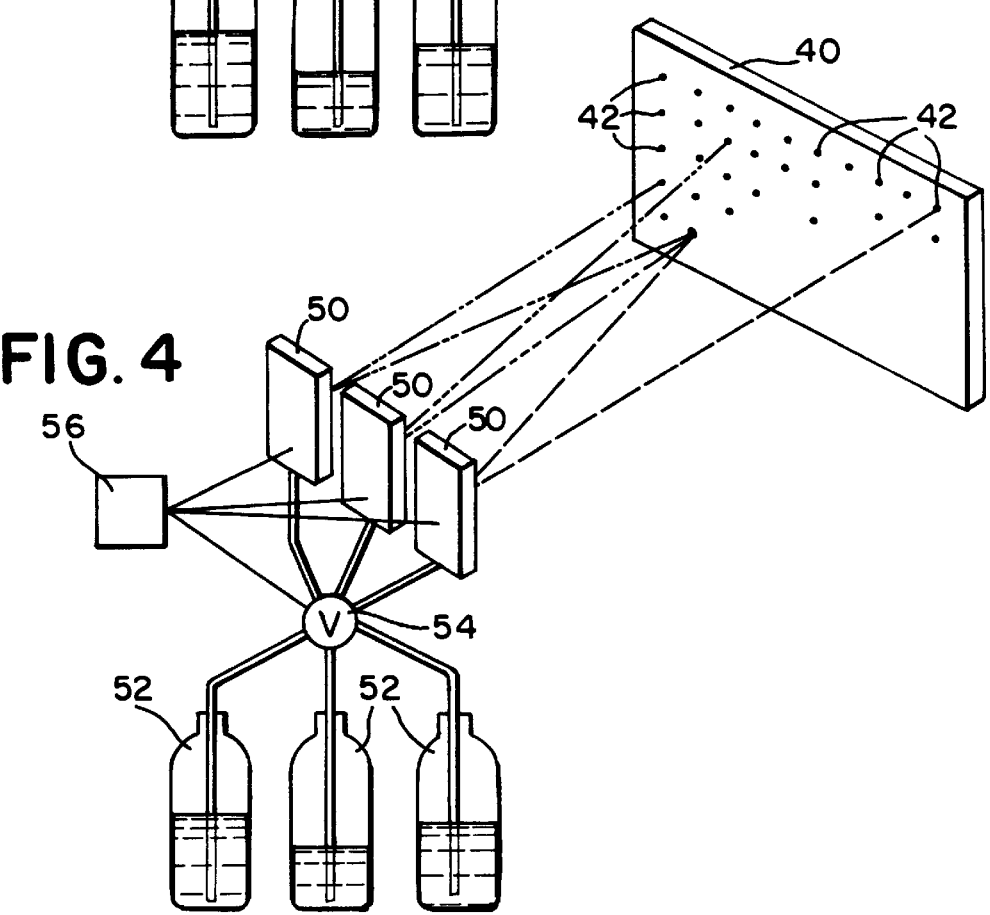
FIG. 4 is a chemical jetting apparatus in schematic, wherein a plurality of chemical droplet generating heads is employed to direct different chemical reagents to sites on a reaction surface.

As shown in FIG. 4, it is possible to avoid the need for all or some of the washing/purging steps which are generally required when pluralities of reagents are jetted from a single head. This may be accomplished in accordance with a further embodiment of the present invention through the employment of a plurality of droplet generators which are each capable of delivering droplets of reagent to reaction sites, 42 on a reaction surface, 40. Thus, a plurality of droplet generators, 50 are provided in fluid communication with reservoirs of chemical reagents, 52 through the mediation of valving means, 54. It is preferred that the droplet generators, 50 and valving means, 54 be under control of a controller, 56 which is preferably either a general purpose digital computer, special purpose digital computer, or specialized controller.

The droplet generators, 50 may preferably be arranged in such a fashion that they can traverse through a space while distributing reagent droplets, however this is not obligatory. It is convenient to employ four jetting heads although other pluralities may be selected. Four is preferred since four head ink jetting systems for color printing purposes are known as are control means therefore.

In accordance with certain preferred embodiments of this invention, composite droplet generators may be employed. A composite droplet generator is one which incorporates a plurality of orifices within one physical structure. Thus, the elements needed to effect a jetting of reagent droplets may be integrated in such a fashion that a plurality of droplet orifices share one or more elements such as reagent reservoirs, pumps, piezoelectric elements and the like. All such modifications are within the spirit of the present invention.

Figure 5:
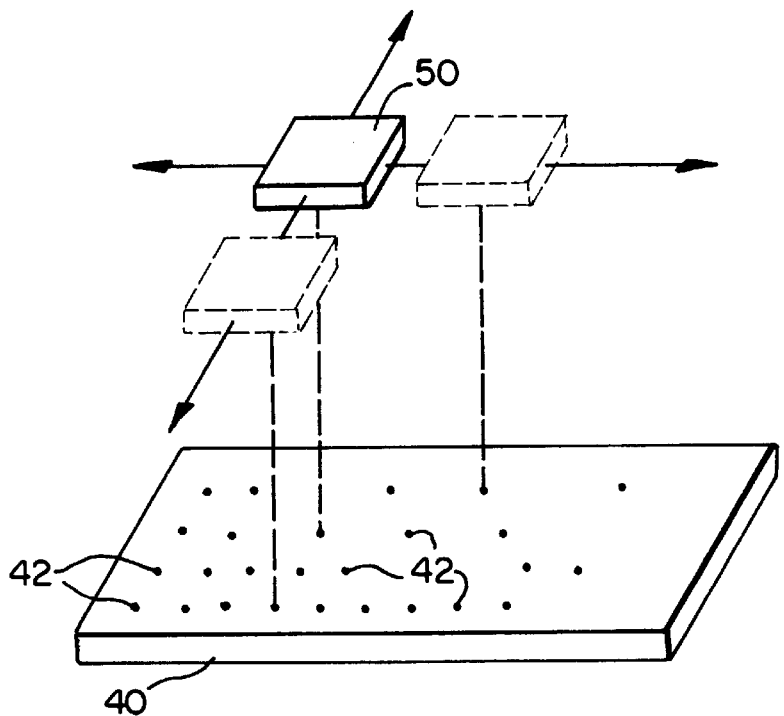
FIG. 5 shows the transitting of a chemical droplet generator over a reaction surface to deposit droplets of reagent at preselected sites on the surface.

FIG. 5 depicts a preferred aspect of the droplet generator relationship to the reaction support. One or more droplet generators, 50 may be caused to be traversable with respect to the surface of the reaction support, 40. Such droplet generators may traverse along one axis or, preferably along two axes in the nature of a plotting device. In such a case, it is not generally necessary to employ electrostatic direction of droplets to reaction sites, rather the transverse movement of the droplet generator can precisely place reagent droplets as required at particular sites, 42. It is preferred that the droplet generators be oriented to direct droplets in a downward direction; the reaction support is preferably oriented horizontally. This permits gravity to assist in the penetration of reagent droplets into the pore volume of preferred reaction surfaces and to aid in transport of liquid through such supports as will be described more completely infra in connection with other preferred embodiments.

In accordance with other embodiments of the present invention, reaction supports are provided which are especially suitable to the practice of the methods of this invention. It will be appreciated that the techniques as described in the present invention serve to deliver droplets of chemical reagents to localized reaction sites on the reaction surface. It has now been found, however, that great advantages may attained by employment of particular reaction substrates having significant internal surface area as reflected by pore volume. Accordingly, it is one aspect of the present invention to employ reaction supports for chemical jetting systems, which reaction supports have significant pore volumes. Such reaction supports are best described by what they do. Their character of porosity leads to their ability to cause droplets of reagent to enter into the body of the substrate, within pores or voids, such that relative large amounts of fluid can be so accommodated. While objects of this invention can be accomplished with reaction supports having relatively little porosity, the larger effective surface areas available from relatively porous substrates is desirable. By employing porous reaction supports in accordance with the present invention, it may be seen that increased volumes of reagent may be delivered to reaction sites on reaction surfaces since the reagent liquid will be absorbed into the pore volume of the reaction support through capillary action, gravity, and otherwise.

It is preferred to employ reaction supports having a porosity such that liquid is capable of passing from the surface upon which reagent impinges to the opposite surface, e.g. the support is at least partly permeable. Examples of such permeable reaction supports include permeable and semipermeable membranes, especially isotropic and anisotropic, polymeric membranes, and control pore glass. Porated membranes and glasses, e.g. having surface which have been subjected to ion nuclear bombardment to effect holes therethrough, and various ceramics are also useful. Such materials are best described by what they do rather than by what they are. Thus, preferred reaction supports are those having a significant pore volume and which are not inconsistent with reaction chemistries to be practiced upon them. Accordingly, employment of a reaction support which reacts with or destroys any of the chemical species which are intended for contact with it would be contraindicated for that particular chemical reaction sequence. It is believed that persons of ordinary skill in the art will have no difficulty in determining appropriate reaction supports in accordance with the foregoing principles.

Exemplary reaction supports for use in accordance with the present invention include CPG (controlled pore glass) available from various distributors including CPG Inc./ Millipore Corp.; RAPP copolymer, a highly crosslinked polystrene, sold as TentaGel or a like product HLP (high loaded polystrene) sold by ABI Corp.; Primer Support, a highly crosslinked polystrene, sold by Pharmacia; POROS-OS polystrene sold by PerSeptive, MPG (a magnetic pore glass) sold by CPG Inc.; Nucleic Acid Membrane Support sold by Millipore. Other useful supports include membranes sold by the Amicon division of W. R. Grace, Inc., and those sold by Gelman Sciences. Polyether sulfone, polysulfone, PVDF, PTFE, PVC, polypropylene and nylon supports may be employed for various applications, as may many other materials.

Other membrane supports include membranes as described or referenced in U.S. Pat. No. 4,923,901 assigned to Millipore Corp.; various supports as described in patent application WO 94/05394 and references cited therein; and various supports as described in patent application WO 90/02749 including activated polystrene layer on a polyethylene membrane. Further Zeolites, cellulose, cottons, other polystyrenes that can optionally be crosslinked, polyacrylamide, which may be optionally crosslinked, latexes, dimethylacrylamide optionally crosslinked with N,N'-bis-acryloylethylenediamine can also be mentioned.

For certain preferred embodiments of the invention, it is preferred that the reaction support possess porosity in such a fashion that indiscriminate blotting or wicking is avoided. Indiscriminate blotting or wicking in this context is defined to mean the wicking away of liquid from the point of impingement of a chemical reagent upon a reaction surface in a direction in other than the direction normal to and through the surface. Thus, it is desired that the reaction supports transmit liquid impinging upon their surface through the body of the support and to the opposite side rather than across the surface or laterally into the body of the support. While, inevitably, some wicking of reagent will occur, it is preferred that the fluid be transmitted predominantly in the normal direction. This concept of wicking is necessarily qualitative, but is believed to be understood by persons of ordinary skill in the art.

Supports which exhibit a diminished tendency towards laterally wicking or blotting and which transmit fluid normal to the surface and through the support, are greatly desired for a number of reasons. First, reliable washing of the support upon which reagent is absorbed can be attained more easily when lateral wicking is avoided. Moreover, when lateral wicking is minimized, reaction sites can be defined more closely together on a surface of a reaction support than if lateral wicking is significant. The selection of reaction supports for use in conjunction with the present invention having diminished tendencies towards lateral wicking while maintaining high internal pore volume permits greater efficiencies in performance of the methods of the present invention. Thus, greater synthetic speed and yield may be evidenced since it is easier to wash the surfaces contacted by the chemical reagents while maintaining a high concentration of reaction sites for reaction.

Capillary glass has been found to be particularly useful for the practice of the present invention. Capillary glass is a material which is known per se and comprises substantially parallel glass filaments oriented in a direction substantially normal to the surface. Various capillary glasses are commercially available such as those that are used for capillary gel electrophoresis. These include both internally coated and uncoated supports available in various internal diameters including 50, 75 and 100$\mu$ that typically have a 365$\mu$ outside diameter. One such support is available for Polymicrotechnologies, Inc. Such materials have effective large internal porosities compared to surface area and have little tendency toward lateral wicking. "Bundles" of such capillary glass filaments are be assembled for use as support of the processes of the invention.

A wide variety of other materials may also be used in accordance with the present invention. The 48 well and the 96 well versions of GibcoBRL's "The Convertible Filtration Manifold System" sold by Life Technologies, Gaithersburg, Md. can be used as separators for reaction area on an appropriate planar membrane such as the above mentioned Nucleic Acid Membrane Support sold by Millipore, Corp. In essence, the filtration manifold defines reaction areas that can be filtered under vacuum to facilitate reagent and solvent removal. The jetting heads of the invention can be used to create a single polymeric species within each of the areas defined by the top plates of these filtration devices or they can be used to create multiple polymeric species within each area. Thus in one embodiment of the invention, such a manifold, as for instance the 96 well manifold, will be used in conjunction with the jetting head of the invention to create 96 individual polymeric species whereas in a further embodiment, the jetting head will deposit, as for instance, as 10 by 10 matrix of individual polymeric species in each well of the manifold to create a total of 9,600 individual polymeric species over the 96 wells of the manifold.

Further preferred support structures of the invention utilize an array of openings in a matrix support material. Such structures can be formed utilizing Helix HD-864-PS-50 or HD-864-PC-50 864 Well High Density Microwell plates (having 864 individual wells, each of a 20 μl volume, located within the foot print size of a normal 96 well microtiter plate available from Helix, San Diego, Calif.) loaded with an appropriate reaction support medium. Each well so modified serves as an individual reaction vessel that can be charged via the jetting device with appropriate reagents, wash solvents and the like.

These same Helix high density microwell plates can be modified by removing the totality of the bottom surface of the plates by machining. This creates a structure having a plurality of parallel capillary tubes suitable of loading with an appropriate reaction support medium. Such modified plates can be used with an appropriate commercial vacuum apparatus such as the above described GibcoBRL Filtration Manifold System from Life Technologies, Gaithersburg, Md. The modified high density microtiter plates are supported on a gasket having a hole pattern that matches the hold pattern of the modified plate. In one embodiment of the invention, strips of the above-noted Nucleic Acid Membrane Support sold by Millipore are rolled, in a manner like a cigar, and are inserted in the so formed capillary tubes. Upon completion of synthesis of the polymeric compounds, the strips can be remove with the polymeric materials still attached and used as such for biological testing. In a further embodiment, the polymeric materials are released from the support membranes and used in solution. Alternately such high density microtiter plates can be modified by the drilling an opening, as for instance a 0.1 to 0.5 mm opening, in the bottom of the individual wells. A porous plug is then located in the bottom of each well and the well loaded with an appropriate support medium.

In a further preferred support, glass whiskers can be repeated sonicated to create porosity therein. Such porous whiskers are then aligned axially and are imbedded in a spaced array in an inert matrix material, as for instance polyethylene, to form a filamentous structure having a plurality of parallel aligned porous glass rods. These porous glass rods can then be derivitized with linkers. Usable as a linker is one of the many linkers known for use with CPG and other glass supports. The linkers, in turn, are used to attach the first monomer unit of a oligomeric compound in the same manner as is practice with common CPG support materials.

Further preferred support materials are anisotropic polymeric membranes. These are known per se and are widely available such as from the Amicon Division of W. R. Grace. Such anisotropic membranes have a first surface with relatively "tight" pores which communicate with increasingly larger pores in the membrane. At the distal surface of the membrane, the pores are quite large and provide no hydraulic impedance of fluid movement. Application of chemical reagent to the tight surface of such membranes, called the skin, with concomitant migration to the large pore volumes just below the surface is highly advantageous in the practice of this invention. Such membranes are available in a large number of chemical forms including polyether sulfones, polysulfones, polyvinylidene fluorides, nylons, PTFEs, acrylics and many others. Such materials generally exhibit a desirably small lateral wicking and are, accordingly, preferred for use in some embodiments of the invention.

Other preferred membrane supports utilizes a polyvinylidene difluoride membrane as described above that is a treated with diaminopropane in DMF e.g. utilizing the procedures of Example 1 of U.S. Pat. No. 4,923,901 to form a polymeric membrane suitable for use to form polynucleotide type oligomers. A further particular preferred membrane, particularly useful for synthesis of peptide and peptide like (peptoid, polycarbamate and the like) polymeric compound libraries, utilizes a polypropylene membrane that is derivitized with hydroxypropylacrylate by coating the polypropylene membrane with crosslinked polyhydroxylproplyacrylate. This membrane was described by Daniels, et. al, in poster #T81 at the Protein Society meeting, San Diego, Calif., 1989. Particularly useful for synthesis of oligonucleotides and the like is a membrane support described by Fitzpatrick, et. al., presented in a paper entitled "Membrane Supports for DNA Synthesis", at the 1993 "Innovations and Perspectives in Solid-Phase Synthesis" conference at the University of Oxford. This support utilizes a PTFE (polytetrafluoroethylene) membrane that is coated with a terpolymer coating consisting of methylene-bisacrylamide, N,N-dimethylacrylamide and aminopropylmethacrylamide. Nitrophenylsuccinates of appropriate first monomeric units are reacted with the primary amine groups of the coating. The density of the growing oligomer is controlled by the spacing of the aminopropylmethacrylamide monomer of the coating. Steric hinderance can be prevented by infrequently incorporating this monomer in the coating.

It will be appreciated that syntheses similar in many chemical respects to existing "solid state" synthesis are preferred for use in connection with some embodiments of this invention. In such cases attachment of an initial reactant, chemical substrate or moiety to a solid, here the reaction surface of the reaction support, is preferred. The materials selected for the reaction support should preferably be capable of functionalization by such an initial chemical moiety. A large variety of appropriate materials are known in this context such as glasses, ceramics, many polymers and other species. Following synthesis, it is generally the case that the synthesized chemical species are conventionally cleaved from the solid and recovered through washing. Selection of reaction supports stable to such practices is greatly preferred.

It is also preferred in some embodiments to effect partial synthesis of chemical species. Thus, for example, oligomers can be elaborated through iterative solid phase chain elongation reactions and then cleaved and recovered. Post processing, such as to remove protecting groups, may then be performed as desired.

A matrix of reaction sites is preferably defined on the surface of the reaction support such sites being intended for the deposition of droplets of chemical reagent. Such sites are not generally marked visibly, but rather are defined geometrically and addressably by the control means for deposition of reagents. Pluralities of sites may be used for the same reaction series or different reactions may occur at each in accordance with the designs of the operator.

In accordance with other embodiments of the invention, chemical reaction apparatuses are provided that are particularly adapted to the present methods. A reaction support having a reaction surface for the desired chemical reactions is provided. A collection plate is also provided, such plate being adapted for lying adjacent to the reaction support at the surface distal from the reaction surface. The collection plate is also preferably provided in such a fashion as to have a plurality of collection wells which are arrayed in a matrix isomorphic with the matrix of reaction sites extant upon the reaction surface of the reaction support. The assembly is such that when a fluid is placed upon the reaction surface of the reaction support at a reaction site thereof, it will pass through the reaction support, arrive at the second surface distal from the first surface, and collect in a well of the collection plate corresponding to the reaction site. It is apparent that the array of reaction sites and collection wells on the collection plate may be structured in any geometric pattern as may be convenient. A rectangular array is convenient and a conventional ninety-six well plate can be used to good effect.

It is also possible and, in some cases preferred, to associate reaction sites with collection wells in a fashion other than one-to-one. For example, a plurality of reaction sites may be identified which are associated with a single collection well on the collection plate. For example, a matrix of reaction sites on the surface of the reaction support may lead to a common collection well. This may be done for a number of reasons including the desire to improve the volume of chemicals processed. A further, and in some cases preferred utility for such an arrangement is to provide libraries of chemical species collected within particular collection wells. Accordingly, a matrix of reaction sites, e.g. a 10×10 matrix, can be associated with a single collection well and the reagents jetted to the 10×10 matrix controlled both as to identity and timing in such a manner as to provide one hundred different chemical moieties to be collected in a single collection well associated with the 10×10 matrix. Since the sequence and identity of chemical reagents jetted to the particular reaction sites is known in all cases, the same having been determined through the programming of the control means, the composition of the chemical library resident in the particular collection well is known with certainty. It is thus possible, in the example given, to assay one hundred chemical species in a particular chemical, biological, or other assay, knowing with certainty the identity of all one hundred chemical species whose performance is to be monitored in the assay. Chemical libraries are inherently useful and valuable. The same are in great commercial demand and should be viewed as a commercially useful article per se.

The foregoing library procedure is of obvious benefit in the screening of new drugs and diagnostics. It is also of great benefit in the identification of chemicals which have agricultural, therapeutical, medicinal, industrial, or other practical uses. Indeed, the present invention provides an unambiguous, rapid, and powerful method for the generation of such libraries without the ambiguity that random synthesis provides. As such, it represents a great advance over prior methods for library creation.

Figure 6:
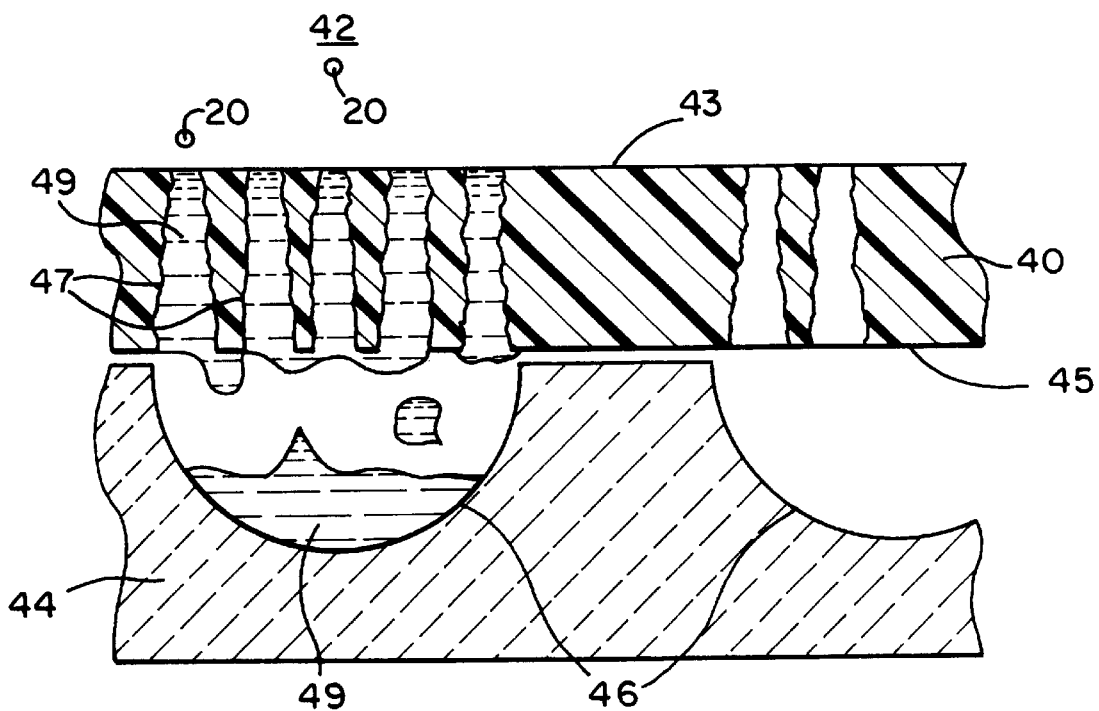
FIG. 6 shows a reaction support surmounting a collection plate and collection wells in the collection plate. The transport of liquid species from the reaction surface to a second surface of the reaction support and its collection into a collection well is shown.

FIG. 6 shows one example of a preferred arrangement. Reaction support, 40 surmounts collection plate 44 having collection wells 46. The reaction surface, 43 of reaction support, 40 is impinged by reagent droplets, 20 at one predefined reaction site, 42 on the reaction surface, 43 of the reaction support, 40. Internal porosity, 47 is shown although the exact geometry of such pores will rarely be known. Such pores or voids may be those from nuclear bombardment from anisotropic synthesis, or as otherwise known or as described herein. In any event, such pores preferably communicate with the second, distal surface, 45 of the reaction support, 40 preferably without undue lateral wicking, such that liquid impinging a particular site, 42 on the reaction surface, 43 of the reaction support will be transported to the collection well, 46 of collection plate, 44 which is isomorphic with such reaction site. Such liquid is indicated, 49.

Figure 7A:
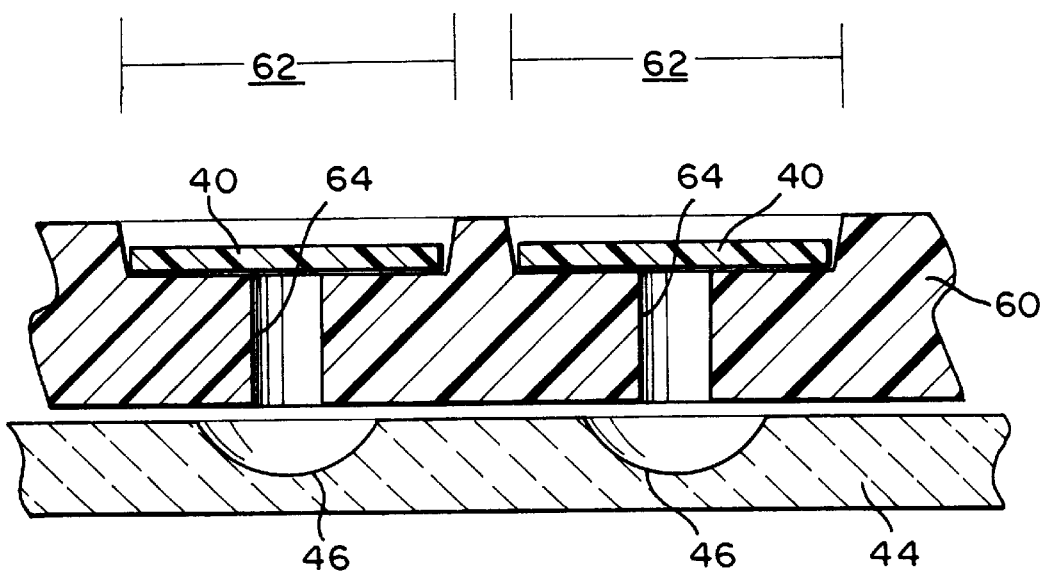
FIG. 7A depicts one embodiment of the invention where reaction wells are formed in a shaped body for holding a reaction support. The wells funnel liquid species transitting the reaction support such that the same may be collected by collection wells of collection plate.
Figure 7B:
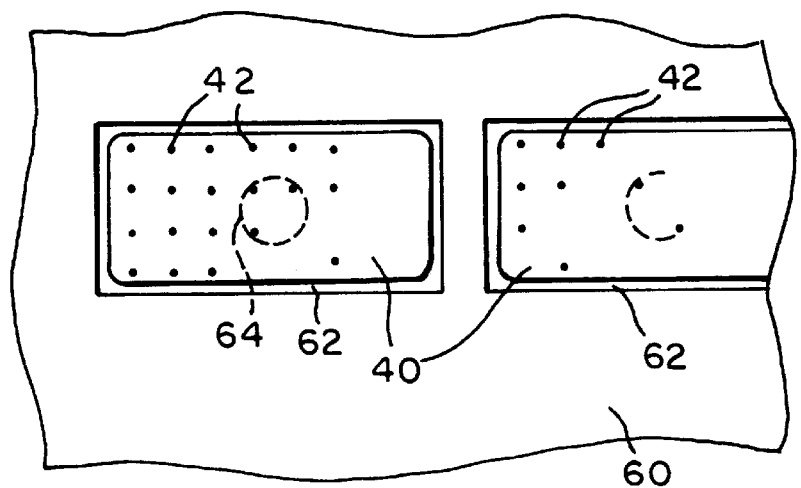
FIG. 7B is a plan view of a portion of a shaped body containing reaction wells and reaction support, the whole suited for surmounting a collection plate.

FIGS. 7A and 7B are cross section and plan views of additional preferred embodiments of this invention. In this embodiment, the reaction support is present in subportions located within reaction wells, 62 on a shaped body, 60. The shaped body is any solid inert with respect to the chemical reactions to take place and capable of appropriate shaping, sterilizing, cleaning and the like as may be desired. Polymer, e.g. nylon or PTFE, glass, ceramic or metal are exemplary materials. The reaction wells, 62 are preferably molded or machined into a surface of the shaped body, 60 in any convenient manner, such as by milling. The reaction wells are preferably in fluid communication with a second surface of the shaped body, and are optionally but preferably adapted to funnel liquid from a larger portion of the well to a smaller or funnel portion, 64. The funnel portions are preferably located to cooperate with collection wells, 46 of a collection plate 44 adapted to lie adjacent the shaped body distal from the reaction wells. Chemical reactions are performed on the reaction support, 40 in each well which can be easily rinsed through the well funnel portions. Following completion of synthesis, the completed chemical species can be directed through the funnel portions for collection in the collection wells. While the apparatus thus described is useful with chemical jetting techniques as set forth herein, other synthetic techniques may also be used therewith.

FIG. 7B shows a plan view of a portion of a shaped body, 60 with one complete well, 62. An array of reaction sites, 42 are shown. The reaction support may be any material herein described or, indeed, any other as may be benefitted from the reaction well and funnel aspects of the invention.

Figure 8:
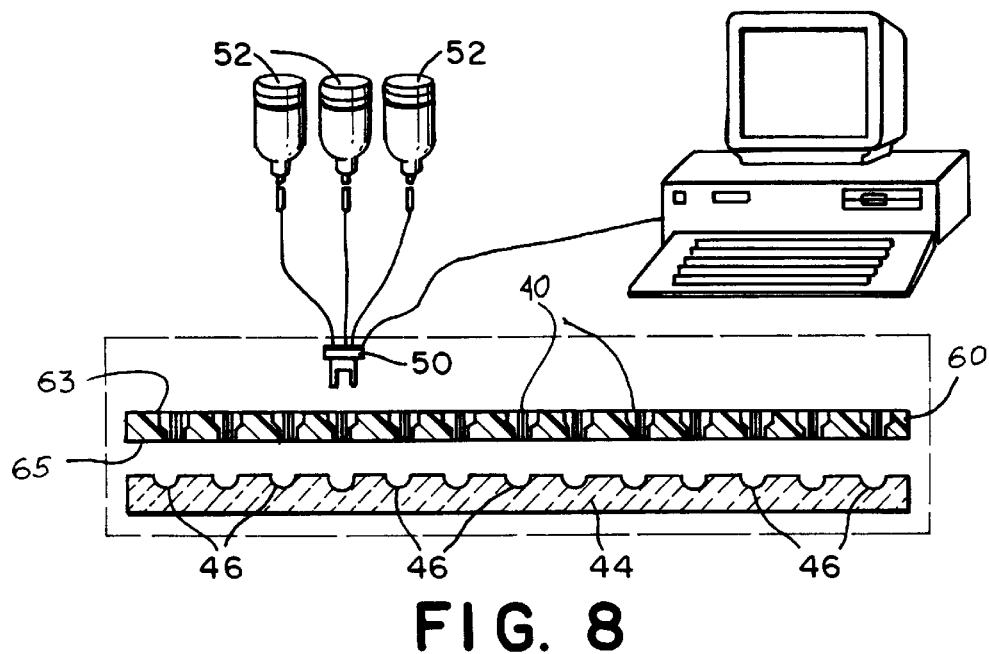
FIG. 8 is a depiction of a preferred apparatus having a transitting droplet generating head together with preferred reactive supports within reaction wells of a shaped body. Collection wells in a collection plate are shown.
Figure 8A:
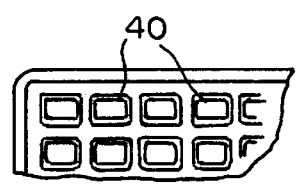
Figure 8B:
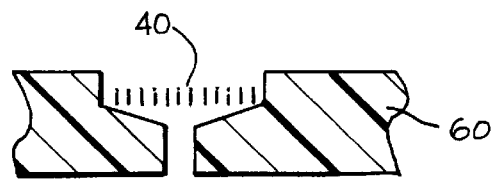
FIG. 8B shows a reaction support within a well.

FIG. 8 is a schematic depiction of one system in accordance with this invention. Chemical droplet generating head, 50, in this depiction attached to a plurality of reagent sources, 52, is arranged to deposit chemical species upon reaction surface, 43, of reaction supports, 40 disposed in reaction wells in first surface, 63 of shaped body, 60. In accordance with this embodiment, pluralities of matrices of reaction sites, here 10×10 sites, shown in FIG. 8A, are defined on the reaction surface of the reaction supports, 40 such that each set of one hundred reaction sites generally communicates with one area on the second, distal surface, 65 of shaped body 60. A collection plate, 44 having collection wells, 46 is also provided in an isomorphic fashion such that, in this example, for each 10×10 matrix of reaction sites leading to a generally common area on the distal surface, 65 of the shaped body, 60, one well is provided into which liquid from the reaction sites can flow in a common fashion. FIG. 8B depicts reaction support, 40 in a well of shaped body, 60.

Throughput of liquid from the reaction sites to the second surface of the reaction support may optionally be encouraged in a number of ways. In accordance with preferred embodiments, a partial vacuum is applied in such a fashion that liquid is extracted from the reaction support. Subsequent washing with an appropriate solvent can ensure complete transfer of material from the reaction support to the collection plate. Alternatively, application of solvent to the reaction sites on the reaction surface of the reaction support will have a washing effect causing translocation of chemical species to the collection wells.

Once the products of the chemical reaction have been transferred to the collection wells, they may be used in further synthesis, may be used per se, may be subjected to one or more assays, or may otherwise be employed in many ways known to persons of ordinary skill in the art.

In accordance with certain preferred embodiments, it is preferred to adapt the apparatus of the present invention so as to direct liquid from the reaction support to the collection wells in as highly efficient a fashion as possible. Thus, the reaction support may be formed of a composite or may be adapted in various ways to encourage this goal. It is within the spirit of the present invention to provide composite supports for elaboration of chemical species. Thus, a shaped body containing pluralities of wells may be elaborated, such wells being shaped so as to effectively funnel liquid from a first surface to a second surface thereof as described above. This arrangement is adapted either to be surmounted by a reaction support where chemical reactions are to take place or to contain in reaction wells, reaction support for such reactions. In any event, the elaboration of appropriately shaped structures facilitates the cooperation of reaction support with collection wells in a collection plate to accomplish preferred goals of the present invention. It will be appreciated that large numbers of variations are possible in this context and all are within the spirit of this invention.

It will be appreciated that these aspects of the invention are not limited by the particular type of chemical synthesis that may be employed and while both single head jetting systems as well as plural head jetting systems are contemplated hereby other reagent application techniques are also comprehended by this invention.

It will also be understood that a wide variety of atmospheres may be imposed upon the synthetic methodologies of the present invention to permit the elaboration of chemically sensitive, corrosive or reactive moieties. Thus, it is often preferred to employ an inert atmosphere, such as argon, and to exclude moisture.

Determination of preferred conditions of time and temperature as well as reagent concentration and catalysis is within the skill of the routineer in the synthetic art. For the synthesis of oligomers, conditions generally similar to those employed in automated synthesis equipment known heretofore provides a useful point of departure from which selection of appropriate conditions may easily be determined for any particular apparatus or method in accordance with this invention.

In accordance with some embodiments it is preferred to orient the synthetic systems such that the effects of gravity may be invoked to transmit liquid from the reaction sites through the reaction support to the second surface of the reaction support for collection in collection wells. It will also be appreciated that evaporation of solvent from the collection wells may be accomplished through the application of gas to permit sequential washing steps and the like to occur without overflowing the collection wells.

Through the use of the collection well embodiments of the present invention, interface of the methodologies of this invention with previously known techniques in chemistry, biotechnology, and other disciplines may be attained. Thus, once predetermined species are known to be present in collection wells of the collection plate, various traditional analytical techniques may be applied. These include testing protocols based upon cell based and biochemical assays. These can be used in association with other techniques such as ELISA assays and the like. Testing protocols can be used to measure various parameters including enzyme/substrate interaction, protein/protein interaction, substrate/transcription factor interaction, ligand/receptor interaction.

A very important use of the present invention is for the generation of highly accurate, libraries of chemical compounds, specially oligomeric libraries. Exemplary uses of such libraries are abundant. Illustrative cell based assays and brief descriptions of the assays are:

HIV—CEM-SS cells are infected with live virus (HIV-1) in presence of library subsets; assay measures protection of the cells by the library subsets from virus-induced cytopathic effects. Tuberculosis Bacteriocidal effects of the library subsets on the mycobacterium are measured.

Tumor Necrosis Factor—Inhibition by library subsets of TNF induction of inflammatory cascade in NHDF cells is monitored using ICAM-1 induction as endpoint.

Interleukin 1-Beta—Inhibition by library of IL1-βinduction of inflammatory cascade in NHDF cells is monitored using ICAM-1 as endpoint.

LPS—Inhibition by library subsets of LPS induction of inflammatory cascade in NHDF cells is monitored using ICAM-1 induction as endpoint.

Malaria—Inhibition of parasite replication in blood cells by library subsets is measured.

Interleukin-6—Inhibition by the library subsets of interaction of IL-6 and its receptor-expressed on live cells is monitored using an antibody specific for IL-6.

MRP/MDR—Enhancement by the library subsets of the toxic effects of chemotherapeutic drugs on mammalian cells expressing either MRP or MDRI is monitored using an MTT assay.

PDGF—Library subset inhibition of the radioactively-labeled ligand interaction with membrane-bound receptor is measured. The membrane is partially purified from guinea pig spleen. Complement $C5_A$ Library subset inhibition of the radioactively-labeled ligand interaction with membrane-bound receptor is measured. The membrane is partially purified from guinea pig spleen.

$LTB_4$ —Library subset inhibition of the radioactively-labeled ligand interaction with membrane-bound receptor is measured. The membrane is partially purified from guinea pig spleen.

$PLA_2$—Library subset inhibition of enzymatic activity of type II phospholipase $A_2$ is measure. The substrate is $E.$ $coli$ with a radioactively-labeled fatty acid in the membrane.

TAT/tar—Biotinylated TAR RNA is bound to streptavidin-coated wells of a 96-well microtiter plate. Inhibition by the library subsets of the interaction of the tat protein with the TAR RNA is monitored in an ELISA-type assay using a tat-specific antibody.

In addition to the above specific uses, other use for the compounds that comprise the libraries of this invention are as general use enzyme inhibitors, additives for foodstuffs, as agent used in affinity chromatography, and as probes and diagnostic agents in kits and the like with or without the addition of suitable labels including fluorescent agent, radioactive agents, or enzymes labels. Other uses will also be apparent.

As will be appreciated, the apparatuses and techniques of the present invention are amenable to a wide variety of chemical and biochemical synthetic schemes. Thus, it is possible to employ nearly any type of chemical reaction save, possibly, those which take place exclusively in the gaseous phase and those which require biphasic catalysis. In general, it is preferred to attach a first species to the reaction surface, both at the actual surface of the reaction support and to a greater or lesser extent at the surface of the internal pore volume, followed by subsequent chemical reactions. It is convenient to attach the first chemical reactant universally over the entire reaction support since the same may be accomplished through immersion of the support in appropriate reactants. Subsequent, dropwise application of reagents effect chemical reactions locally at the reaction sites under the control of control means. It is also possible and in many applications preferred, to perform all reactions in a dropwise fashion through chemical jetting.

Oligomers are preferred species for synthesis in accordance with the present invention. Thus, oligonucleotides, polypeptides, and oligosaccharides may be so synthesized.

Such oligomers may be either synthesized in relative bulk, where many or all of the reaction sites are caused to experience the same reaction conditions and to lead to the same reaction products, or may be individually determined for subsets of reaction sites.

In accordance with other embodiments, it is preferred to employ the apparatuses and methods of the present invention to prepare nonoligomeric chemical moieties. Thus, "classical" chemistry may be employed to synthesize such chemicals either "in bulk" or with different chemical species being synthesized at different subsets of reaction sites. While it is preferred in some cases to physically attach the developing chemical moiety to the reaction surfaces during the course of synthesis, it is also possible in some embodiments to avoid this step. In such case, it is generally preferred to effect careful reaction and washing conditions so as to retain the intermediate chemical species on the surface for further reaction. This may generally be done through careful selection of the reaction support, chemical reagents, and washing solvents in view of the molecules to be synthesized. Persons of ordinary skill in the art will know how to effect such selections in view of the objects to be attained in particular synthesis.

It is believed to be possible to effect asymmetric synthesis through employment of the present invention. If a chiral synthetic support is adopted, in some circumstances growing chemical intermediates will adopt preferred stereochemical configurations leading to the synthesis of one enantiomer over another without the use of chiral reagents. The asymmetric synthesis of chemical species on asymmetric surfaces is known per se and such techniques may be adopted here. The methods of the invention may be used to produce oligomeric species having a variety of different monomeric subunits. Thus, the methods of the invention may advantageously be employed in the synthesis of polymers of nucleotides (oligonucleotides or nucleic acids), peptides, proteins, peptide nucleic acids (PNAs), and other polymeric species synthesizable by iterative addition of synthons to adducts on the reaction surface.

Synthetic techniques such as solid phase peptide synthesis and solid phase nucleic acid synthesis utilize the ability to selectively protect and deprotect specific functional groupings. Protecting groups are conveniently characterized as either "temporary" or "permanent." "Temporary" protecting groups are quantitatively removed at each step of the synthesis to allow coupling of the next synthon. "Permanent" protecting groups are stable to the conditions of the iterative elongation cycle, and therefore protect side chain, nucleobase, or other functional groups which do not participate in, but may interfere with chain elongation. Typically, permanent protecting groups are chosen such that conditions required for their removal are equivalent to those required for cleavage of the completed chain from the reaction support, affording concomitant removal.

The methods of the present invention may be used to synthesize peptides by standard solid phase peptide synthesis (SPPS) methodologies (see, e.g., Merrifield, *J. Am. Chem. Soc.*, 1963, 85, 2149 and *Science*, 1986, 232, 341). Media suitable for use as reaction supports in connection with peptide and synthetic applications of the invention include aminomethyl polystyrene resins, various polyamide support materials, membranes, cotton and other carbohydrates, controlled-pore silica glass, and other media known to those in the art for use in peptide synthesis as solid supports. See *Synthetic Peptides A Users Guide*, Gregory A. Grant, Ed. Oxford University Press 1992.

The initial functionalization of the reaction support may be achieved by any of the more than fifty methods which have been described in connection with traditional solid-phase peptide synthesis (see, e.g., Barany and Merrifield in *"The Peptides"* Vol. 2, Academic Press, New York, 1979, pp. 1–284, and Stewart and Young, *"Solid Phase Peptide Synthesis"*, 2nd Ed., Pierce Chemical Company, Illinois., 1984).

Typically, SPPS (solid phase peptide synthesis) is performed in the "C to N" direction. Thus, anchoring linkers are designed such that cleavage at the end of the synthetic regime produces a C-terminal acid or amide. In preferred embodiments a linker containing an activated carboxyl group is keyed to amino groups on the reaction support. In some preferred embodiments of the invention protected amino acid derivatives having linkers attached (so called "preformed handles") are keyed to the reaction support. See *Synthetic Peptides A Users Guide*, supra, at pages 105–119.

Any of the several "temporary" protecting groups routinely used in the art are suitable for use in the present invention. Preferred among these are the widely used BOC (t-butoxycarbonyl) and FMOC ($N^{\alpha}$-9-fluorenylmethyloxycarbonyl) groups. Other suitable amino protecting groups include 2-(4-biphenyl) propyl[2] oxycarbonyl (Bpoc), 2-(3,5,-dimethoxyphenyl) propyl[2] oxycarbonyl (Ddz), 1-(1-adamantyl)-1-methylethoxycarbonyl (Adpoc) and 4-methoxybenzyloxycarbonyl (Moz). Other suitable protecting groups will be apparent to those skilled in the art, based on their experience and knowledge.

After keying of a linker and/or first monomeric synthon to the reaction support, the iterative process of chain elongation occurs. This may proceed, in accordance with the invention, by any of the several methods known in the art for the formation of peptide bonds. Representative of such methods are the use of in situ coupling reagents, active esters, preformed symmetrical anhydrides and acid halides.

Representative in situ coupling reagents suitable for use in the present invention include N,N'-dicyclohexylcarbodiimide (DCC), and N,N'-diisopropylcarbodiimide (DIPCDI), especially in conjunction with the use of scavenging agents (so called accelerators or additives) such as 1-hydroxybenzotriazole (HOBt), benzotriazol-1-yl-oxy-tris(dimethylamino)phosphonium hexafluorophosphate (BOP), and2-(1H-benzotriazol-1-yl)-1,1,3,3-tetramethyluronium hexafluorophosphate (HBTU). A list of suitable in situ coupling agents may be found in Synthetic Peptides A Users Guide, supra.

Appropriately selected sites on the first surface of a reaction support are jetted with a solvent as a washing or rinsing step, and then the temporary protecting group on the terminal synthon is cleaved by jetting a deprotection reagent onto the preselected sites of the reaction support. This is optionally followed by the jetting of one or more conventional rinsing reagents. The next protected monomeric synthon is then jetted in a suitable solvent such as dimethyl formamide. Coupling or activating agents, including accelerators or additives such as HOBt, optionally may be jetted with the protected monomeric synthon or alternatively may be jetted independently in an appropriate solvent.

After a suitable reaction time, the iterative cycle is repeated until the desired amino acid sequence is achieved. Cleavage of the completed product from the reaction support is achieved by jetting a cleaving reagent onto the reaction support surface. The cleaving reagent also typically functions to remove the "permanent" protecting groups from the amino acid side chains. Choice of a specific cleavage reagent will necessarily be determined by the particular synthetic chemistry employed. For example, Boc SPPS chemistry will typically employ strong acid such as hydrogen fluoride for cleavage, while in Fmoc SPPS chemistry, the same result is typically accomplished with trifluoroacetic acid. See *Synthetic Peptides A Users Guide*, supra, at pages 130–136.

The methods on the invention may similarly be employed in the synthesis of non-peptide polymeric species which consist of monomers linked by traditional peptide chemistries. Representative of these species are peptide nucleic acids (PNAs), which are disclosed in WO 92/20702. In PNAs ligands are linked to a polyamide backbone through aza nitrogen atoms. U.S. application Ser. No. 08/054,363, filed Apr. 26, 1993 and a corresponding PCT Application PCT/IB94/00142 filed Apr. 25, 1994 discloses peptide nucleic acids in which their recognition moieties are linked to the polyamide backbone additionally through amido and/or ureido tethers. Additional PNAs and methods for their synthesis are also disclosed in U.S. application Ser. No. 08/088,658, filed Jul. 2, 1993 and a corresponding PCT Application PCT/US94/07319 filed Jul. 2, 1994.

These PNAs are synthesized by adaptation of standard peptide synthesis procedures. The synthons used are unique monomer amino acids or their activated derivatives, which are protected by standard protecting groups. Thus, the synthesis of these PNAs may be accomplished according to the methods of the present invention in similar fashion to protocols specified above for synthesis of peptides.

For example, the reaction support may be functionalized according to methodologies specified above to incorporate Boc-L-Lys(2-chlorobenyloxycarbonyl). An excess of a desired monomer to be coupled may be jetted on the reaction support, followed by jetting of a coupling reagent such as dicyclohexylcarbodiimide in a suitable solvent such as 50% DMF in dichloromethane. Boc deprotection may then be accomplished by jetting of trifluoroacetic acid. After completion of the desired chain, the PNA may be cleaved from the reaction support by jetting of a mixture of trifluoromethanesulfonic acid:trifluoroacetic acid: meta-cresol (1:8:1 v:v:v). The product is precipitated from the solution by the addition of diethyl ether.

The methods of the present invention may be advantageously employed to synthesize deoxyribonucleic acid (DNA) or ribonucleic acid (RNA) (together "oligonucleotide") species by any of the several chemistries for solid phase DNA or RNA synthesis, including phosphite triester, (phosphoramidite) synthesis and H-phosphonate synthesis. See *Nucleic Acids in Chemistry and Biology*, M. Blackburn and M. Gait, Eds., IRL Press 1990, at pages 112–130. In principle, the methods of the present invention will be useful in the practice of any iterative nucleic acid synthetic technique. In preferred embodiments of the invention oligonucleotides are synthesized by the phosphoramidite method. Representative solid-phase synthetic methodologies useful in the present invention may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Media suitable for use as reaction supports in connection with oligonucleotide synthetic applications of the invention include controlled-pore silica glass (CPG); oxalyl-controlled pore glass (see, e.g., Alul, et al., *Nucleic Acids Research* 1991, 19, 1527); RAPP copolymer highly crosslinked polystyrene, TENTAGEL Support, (see, e.g., Wright, et al., *Tetrahedron Letters* 1993, 34, 3373); HLP, a high loaded polystrene available from ABI; POROS, a polystyrene resin available from Perceptive Biosystems, and other media known to those in the art for use in oligonucleotide synthesis as solid supports.

For phosphoramidite synthesis according to the invention, the reaction support is preferably functionalized with spacer groups according to methods known in the art. Typical of such spacer groups are long chain alkylamines. The spacer groups may be keyed to preselected portions of the reaction support, or to the entire reaction support surface.

Keying of the initial monomeric synthon may be accomplished by jetting appropriately derivitized nucleoside monomers (having protecting groups on any exocyclic amine functionalities present) onto the reaction support. For example, a 5'-O-DMT-3'-O-(4-nitrophenyl) succinate monomer may be jetted onto the reaction support, keying the initial monomer to the reaction support through the alkylamine spacer. Typically, monomeric synthons bear temporary protecting groups at appropriate nucleobase or 2'-O positions. See *Nucleic Acids in Chemistry and Biology*, supra.

Solid phase nucleic acid synthetic techniques employ "temporary" and "permanent" protecting groups in analogous fashion to solid phase peptide synthesis. Base labile protecting groups are used to protect the exocyclic amino groups of the heterocyclic nucleobases during the synthesis. This type of protection is generally achieved by acylation with acylating reagents such as benzoylchloride and isobutyrylchloride. Acid labile protecting groups are used to protect the nucleotide 5' hydroxyl during synthesis. Representative hydroxyl protecting groups commonly used in the art may be found in Beaucage, et al., *Tetrahedron* 1992, 48, 2223. These include the dimethoxytrityl, monomethoxy trityl, trityl, and 9-phenyl-xanthene (pixyl) groups. Dimethoxytrityl protecting groups are widely used owing to their great acid lability, which affords efficient removal by dilute acid (e.g. 3% trichloroacetic acid).

The first step in the iterative chain elongation cycle according to the phosphoramidite technique is the removal 5'-O-protecting group (deprotection) of the initial monomer by jetting an appropriate deprotecting reagent onto the preselected portions of the reaction support. This is followed by the jetting of a rinsing reagent. Suitable reagents for deprotection include Lewis acids such as $ZnBr_2$, $AlCl_3$, $BF_3$ and $TiCl_4$ in solvents such as nitromethane, tetrahydrofuran, and mixed solvents such as nitromethane and lower alkyl alcohols, such as methanol. Protic acids such as acetic acid, dichloroacetic acid, trifluoroacetic acid, and toluenesulfonic acid may also be used in an appropriate solvent, typically dichloromethane.

Chains are lengthened by jetting and reaction of activated 5'-O-protected monomeric synthons. In the phosphoramidite technique a 5'-DMTr-deoxynucleoside-3'-O-(N,N-diisopropylamino)-β-cyanoethylphosphite is jetted onto the reaction support. Phosphoramidites of numerous nucleosides are commercially available (for example, from Applied Biosystems Inc. and Millipore Corp.).

A mild organic acid catalyst, typically tetrazole, is jetted onto the reaction support either together with the phosphoramidite or independently thereafter. Commonly used commercially available activating agents are disclosed in U.S. Pat. No. 4,725,677 and in Berner, S., Muhlegger, K., and Seliger, H., *Nucleic Acids Research* 1989, 17:853; Dahl, B. H., Nielsen, J. and Dahl, O., *Nucleic Acids Research* 1987, 15:1729; and Nielson, J. Marugg, J. E., Van Boom, J. H., Honnens, J., Taagaard, M. and Dahl, O, *J. Chem. Research* 1986, 26, all of which are herein incorporated by reference. The coupling reaction is followed by the jetting of a rinsing solvent, typically anhydrous acetonitrile.

After rinsing, a capping reagent is jetted onto the preselected portions of the reaction support to cap free hydroxyl species remaining due to incomplete reaction of phosphite monomers. The capping reagent, which is typically a solution of an acid anhydride, also functions to reverse any inadvertent phosphitylation of guanine O-6 positions.

Oxidation of the resulting phosphite triester to the corresponding phosphate triester may be accomplished by jetting oxidants known in the art to be suitable, such as a solution of alkaline Iodine.

The methods of the present invention may be employed in the synthesis of oligonucleotides having the naturally occurring nucleobases adenine (A), thymine (T), guanine (G), cytosine (C) and uracil (U), as well as non-naturally occurring nucleobases. Non-naturally occurring nucleobases are molecular moieties which are known in the art to mimic the function of naturally occurring nucleobases in their biological role as components of nucleic acids. Examples of non-naturally occurring nucleobases are disclosed in, for example, *Antisense Research and Applications*, Crooke and Lebleu, eds., CRC Press, Boca Raton, 1993.

Further details of methods useful for preparing oligonucleotides may be found in Sekine, M., etc al., *J. Org. Chem.*, 1979, 44, 2325; Dahl, O., *Sulfur Reports*, 1991, 11, 167–192; Kresse, J., et.al., *Nucleic Acids Research*, 1975, 2, 1–9; Eckstein, F., *Ann. Rev. Biochem.*, 1985, 54, 367–402; and Yau, E. K. U.S. Pat. No. 5,210,264 entitled "S-(2,4-Dichlorobenzyl)-β-Cyanoethyl Phosphorothioate Diester".

Oligonucleotide species having a wide variety of modifications to nucleobases, sugars, or inter-sugar linkages can be prepared in accordance with the methods of the invention, which are generally applicable to the synthesis of any oligomer synthesizable by solid phase techniques. For example, the methods of the present invention may be employed in the synthesis of S-phosphorodithioates, phosphorothioates, methyl phosphonates, phosphoramidates, phosphorotriesters, thiophosphotriesters, thiophosphoramidates, methylphosphonothioates, and cyclic phosphorothioates, phosphorothioates, and phosphorodithioates. These modifications are disclosed as set forth in *Antisense Research and Applications*, supra, and in U.S. patent applications assigned to a common assignee hereof, entitled "Backbone Modified Oligonucleotide Analogs," Ser. No. 703,619 and "Heteroatomic Oligonucleotide Linkages," Ser. No. 903,160, the disclosures of which are incorporated herein by reference.

The polymers produced according to the methods of the invention may be composed of more than one type of monomeric subunit (e.g., amino acids, peptide nucleic acids, nucleotides, sugars, etc) and may possess more than one type of inter-subunit. linkage. Illustrative polymers produced according to the methods of the invention include peptides, peptoids (N-alkylated glycines), α-polyesters, polythioamides, N-hydroxy amino acids, β-esters, polysulfonamides, N-alkylates polysulfonamides, sulfonamides, polyureas, urethanes, peptide nucleic acids, nucleotide, polysaccharides, polycarbonates, oligonucleotide, oligonucleosides and the like and chimeric molecules that contain one or more of these polymers joined together as a single macro-molecule.

Libraries of monomeric analog species can also prepared by the methods of the invention. These include benzodiazepine libraries and other such analog libraries including, but not limited to, antihypertensive agents, e.g. enalapril, β-blockers, e.g. proproanol; antiulcer drugs ($H_2$-receptor antagonists) e.g. cimetidine and ranitidine; antifungal agents (cholesterol-demethylase inhibitors, e.g. isoconazole; anxiolytics, e.g. diazepam; analgesics, e.g. aspirin, phenacetamide, and fentanyl; antibiotics, e.g. vancomycin, penicillin and cephalosporin; antiinflammatories, e.g. cortisone; contractives, e.g. progestins; abortifacients, e.g. RU-456; antihistamines, e.g. chlorphenamine; antitussives, e.g. codeine; sedatives, e.g. barbitol and well as many others that will be suggested by this disclosure. Illustrative are the benzodiazepine and the hetero-Diels-Alder libraries as described in published PCT application WO 94/08051; the benzodiazepine and prostaglandins described in U.S. Pat. No. 5,288,514; the dipeptides, hydantoins, benzodiazepins, quinolones, keto-ureas, benzamido-5-oxopentanoic acids, diketopeperazines, 2H-pyranones, N-aryl piperazines, benzoisothiazolones, spirosuccimides, pilocarpine analogs, benzopyrans, pyrimidinediones and tepoxalin analogs described in U.S. Pat. No. 5,324,483.

EXAMPLES

Example 1

Synthesis of Library of Compounds Incorporating $P^V$ Linkages Reagents

Abbreviations and Definitions:

| | |
|---|---|
| DCM | dichloromethane |
| Deblocking agent | 3% trichloroacetic acid in DCM |
| ACN | acetonitrile |
| 1st Capping Sol. | N-methylimidazole |
| 2nd Capping Sol. | acetic anhydride |
| Oxidizer | Iodine for (P=O) or Beaucage reagent for (P=S) |
| Activator | 1-H-tetrazole |
| Amidite | One of various reactant species activated as a phosphoramidite |
| Position set | A predetermined set of positions where a reaction is to take place - may vary for one to all positions wherein jetting head is targeted to dispense reagents |
| All positions | Every position where jetting head is targeted to dispense reagents |

Support:

Membrane Carrier: Membrane strips are positioned on the base plate and gasket and overlaid with the top plate of a 96 well, 6-mm dot GibcoBRL "The Convertible Filtration Manifold System" device from Life Technologies, Gaithersburg, Md. The "well" vacuum line of the carrier is modified to include an electromechanical in line off-on value for control of the vacuum below the membranes. The membrane carrier is located vertically below a droplet generator for jetting reagent droplets. Actuation of the in line vacuum value is via the controller 32.

Cycle:
1. Deliver deblocking agent to all positions on the support
2. Wait 30 seconds
3. Remove by vacuum
4. Deliver ACN to all positions and remove by vacuum
5. Repeat step 4 five times
6. Deliver amidite A to first designated position set
7. Deliver activator to same designated position set
8. Wait 1–5 minutes as required for current amidite being used
9. Remove amidite and activator by vacuum
10. Deliver ACN to same designated position set
11. Remove by vacuum
12. Repeat steps 6–11 for further amidite B to second designated position set, amidite C to third designated position set, etc. for further amidites at designated position sets
13. Deliver ACN to all positions and remove by vacuum
14. Deliver 1st and 2nd capping solutions to all positions 15. Wait 30 seconds
16. Remove by vacuum
17. Deliver ACN to all positions and remove by vacuum
18. Repeat step 15 five times
19. Deliver oxidizer to all positions
20. Wait 30 seconds
21. Deliver ACN to all positions and remove by vacuum
22. Repeat step 19 five times The cycle is repeated n times to achieve oligomer n residues long.

Example 2

Synthesis of Library of Compounds Incorporating Amide Linkages—BOC Chemistry

Regents, Abbreviations and Definitions:

| | |
|---|---|
| DCM | dichloromethane |
| DMF | dimethylforamide |
| TFA | trifluorcacetic acid |
| HATU | O-(7-azabenzotriazol-1-yl)-1,1,2,2-tetramethyl uronium hexafluorophosphate |
| MDCHA | N-methyldicyclohexylamine |
| Deblocking agent | TFA/m-cresol, 95/5, v/v |
| Cap | acetic anhydride/collidine/DMF, 5/6/89, v/v/v |
| Pyridine | Pyridine/DMF, 5/95, v/v |
| Piperdine | Piperdine/DMF, 5/95, v,v |
| Activator A | 0.18 M HATU in DMF, 855 mg plus 12 mL DMF |
| Activator B | 0.3 M HATU in DMF, 570 mg plus 4.7 mL DMF |
| Position set | A predetermined set of positions where a reaction is to take place - may vary for one to all positions wherein jetting head is targeted to dispense reagents |
| All positions | Every position where jetting head is targeted to dispense reagents |
| Monomers | One of various reactant species capable of being linked together via amide linkages |

Support:

Membrane Carrier: Membrane are strips positioned on the base plate and gasket and overlaid with the top plate of a 96 well, 6-mm dot GibcoBRL "The Convertible Filtration Manifold System" device from Life Technologies, Gaithersburg, Md. The "well" vacuum line of the carrier is modified to include an electromechanical in line off-on value for control of the vacuum below the membranes. The membrane carrier is located vertically below with the jetting head. Actuation of the in line vacuum value is via the controller 32.

Cycle:
1. Deliver DMF/DCM to all positions and remove by vacuum
2. Wait 10 seconds
3. Deliver TFA to all positions
4. Wait 10 seconds
5. Deliver TFA to all positions
6. Wait 180 seconds
7. Deliver TFA to all positions
8. Wait 180 seconds
9. Remove by vacuum
10. Deliver DMF/DCM wash and remove by vacuum
11. Deliver pyridine to all positions
12. Deliver DMF/DCM to all positions
13. Deliver monomer A and HATU activator to first designated position set
14. Wait 840 seconds
15. Deliver DMF/DCM wash to first designated position set
16. Remove by vacuum
17. Repeat, in parallel, steps 13–16 for further monomer B to second designed position set, etc. for further monomers at designated position sets
18. Deliver DMF/DCM wash to all positions
19. Deliver cap to all positions
20. Wait 300 seconds
21. Deliver piperidine/DMF to all positions
22. Wait 60 seconds
23. Remove by vacuum
24. Deliver DMF/DCM wash to all positions and remove by vacuum The cycle is repeated n times to achieve oligomer n-residues long.

Optional cleavage of library compounds from support is effected using a cleavage cocktail of m-cresol/thioanisole/TFMSA/TFA, 1/1/2/6, v/v/v/v. The membrane is treated with the cleavage cocktail for one hour followed by removal from the membrane by vacuum into individual wells of an appropriate matrix collection plate.

Example 3

Synthesis of Library of Compounds Incorporating Amide Linkages—FMOC chemistry

Regents, Abbreviations and Definitions:

| | |
|---|---|
| DCM | dichloromethane |
| DMF | dimethylforamide |
| TFA | trifluoracetic acid |
| HATU | O-(7-azabenzotriazol-1-yl)-1,1,2,2-tetramethyluronium hexafluorophosphate |
| MDCHA | N-methyldicyclohexylamine |
| Deblocking agent | 20% piperdine in DMF |
| Cap | acetic anhydride/collidine/DMF, 5/6/89, v/v/v |
| Pyridine | Pyridine/DMF, 5/95, v/v |
| Piperdine | Piperdine/DMF, 5/95, v,v |
| Activator A | 0.18 M HATU in DMF, 855 mg plus 12 Ml DMF |
| Activator B | 0.3 M HATU in DMF, 570 mg plus 4.7 Ml DMF |
| Position set | A predetermined set of positions where a reaction is to take place - may vary for one to all positions wherein jetting head is targeted to dispense reagents |
| All positions | Every position where jetting head is targeted to dispense reagents |
| Monomers | One of various reactant species capable cf being linked together via amide linkages |

Support:

Membrane Carrier: Membrane are strips positioned on the base plate and gasket and overlaid with the top plate of a 96 well, 6-mm dot GibcoBRL "The Convertible Filtration Manifold System" device from Life Technologies, Gaithersburg, Md. The "well" vacuum line of the carrier is modified to include an electromechanical in line off-on value for control of the vacuum below the membranes. The membrane carrier is located vertically below with the jetting head. Actuation of the in line vacuum value is via the controller 32.

Cycle:
1. Deliver DMF/DCM to all positions and remove by vacuum
2. Wait 10 seconds
3. Deliver TFA to all positions
4. Wait 10 seconds
5. Deliver TFA to all positions
6. Wait 180 seconds
7. Deliver TFA to all positions
8. Wait 180 seconds
9. Remove by vacuum
10. Deliver DMF/DCM wash and remove by vacuum
11. Deliver pyridine to all positions
12. Deliver DMF/DCM to all positions 13. Deliver monomer A and HATU activator to first designated position set
14. Wait 840 seconds
15. Deliver DMF/DCM wash to first designated position set
16. Remove by vacuum
17. Repeat, in parallel, steps 13–16 for further monomer B to second designed position set, etc. for further monomers at designated position sets
18. Deliver DMF/DCM wash to all positions
19. Deliver cap to all positions
20. Wait 300 seconds
21. Deliver piperidine/DMF to all positions
22. Wait 60 seconds
23. Remove by vacuum
24. Deliver DMF/DCM wash to all positions and remove by vacuum
25. Repeat cycle by starting at step 13

The cycle is repeated n times from step 13 to achieve oligomer n-residues long.

Optional cleavage of library compounds from support is effected using a cleavage cocktail of 95% trifluoroacetic acid containing 5% scavenger. The membrane is treated with the cleavage cocktail for one hour followed by removal from the membrane by vacuum into individual wells of the matrix collection plate.

Example 4

Synthesis of Library of Compounds Incorporating Hydroxylamine Linkages

Regents, Abbreviations and Definitions:

| | |
|---|---|
| DCM | dichloromethane |
| Deblocking agent | 3% N-methyl hydrazine in DCM:methanol (9:1, v:v) |
| GAA | Glacial Acetic Acid |
| Reducing reagent | NaCNBH$_3$ |
| Alkylating reagent | 20% Formaldehyde |
| TBAF | Tetrabutylammonium fluoride |
| THF | Tetrahydrofuran |
| Intermediate Monomer | One of various 5'-O-phthalimido-3'-C-aldehydo-3'-deoxynucleosides |
| First Monomer | One of various 5'-O-phthalimido-3'-O-(succinyl) nucleosides |
| Final Monomer | One of various 5'-t-butyldiphenylsilyl-3'-aldehyde-3'-deoxy nucleosides |
| Membrane activator | Pentachlorophenol |
| Position set | A predetermined set of positions where a reaction is to take place - may vary for one to all positions wherein jetting head is targeted to dispense reagents |
| All positions | Every position where jetting head is targeted to dispense reagents |

Support:

Membrane Carrier: Membrane strips are positioned on the base plate and gasket and overlaid with the top plate of a 96-well, 6-mm dot GibcoBRL "The Convertible Filtration Manifold System" device from Life Technologies, Gaithersburg, Md. The "well" vacuum line of the carrier is modified to include an electromechanical in line off-on value for control of the vacuum below the membranes. The membrane carrier is located vertically below with the jetting head. Actuation of the in line vacuum value is via the controller 32.

Cycle:
1. Deliver DCM solution of First Monomer A and Membrane activator to a first designated position set
2. Wait 15 seconds
3. Wash with DCM and remove by vacuum
4. Repeat steps 1–3 for further First Monomer B to second designated position set, etc for further First Monomers to designated position sets
5. Deliver Deblocking agent to a first designated position set
6. Wait 120 seconds
7. Wash with DCM for 240 seconds and remove by vacuum
8. Deliver a DCM solution of a selected Intermediate monomer and GAA to this first designated position set
9. Wait 60 seconds
10. Wash with DCM and remove by vacuum
11. Repeat steps 5 to 10 for further Intermediate monomer B to second designated position set, etc for further Intermediate monomers to designated position sets
12. Repeat steps 5 to 11 n–2 times for oligomer n-residues long
13. Deliver a DCM solution of a first Final monomer to a first designated position set
14. Wait 60 seconds
15. Wash with DCM and remove by vacuum
16. Repeat steps 13 to 15 for further Final monomer B to second designated position set, etc for further Intermediate monomers to designated position sets
17. Wash with DCM and remove by vacuum
18. Deliver mixture of Reducing agent, Alkylating reagent and GAA to all positions
19. Wait 180 seconds
20. Wash with DCM and remove by vacuum
21. Deliver TBAF in THF at all positions to de-block all Final nucleosides
22. Wait 30 seconds
23. Wash with DCM and remove by vacuum The oligomers are removed from membrane by treating with 30% ammonium hydroxide.

Example 5

Synthesis of Peptide Nucleic Acid Library

A library of peptide nucleic acids, wherein individual peptide nucleic acid are 6-mers, is synthesizer utilizing the protocol of Example 2. Four nucleobase monomers are used in construction the library. The monomers incorporate normal nucleobases attached to the peptide nucleic acid backbone wherein A is an adenine peptide nucleic acid monomer, G is a guanine peptide nucleic acid monomer, C is a cytosine nucleic acid monomer and T is a thymine nucleic acid monomer. The monomers are used at a 0.2M concentration. BOC (terminal amine groups) and Z (nucleobases) protection is utilized. The monomers and HATU are purchased from Millipore Corp., Bedford, Mass. The membrane is crosslinked PEPS film that is aminomethylated. The aminomethylated film is further modified with a BOC-Try(BrZ) Pam linder from Star Chemicals coupled as a preformed HOBt ester at about 0.15 mmol amino groups per gram of film with the remaining amino groups capped by acetylation with acetic anhydride.

Monomers (0.2 M monomer, 0.2 M MDCHA and 0.3 M collidine)

| Monomer | Weight (mg) | MDCHA ($\mu$l) | collidine ($\mu$L) | Solvent (mL) |
|---|---|---|---|---|
| A | 528 | 214 | 198 | 4.3 |
| G | 544 | 214 | 198 | 4.3 |
| T | 384 | 214 | 198 | 4.3 |
| C | 504 | 214 | 198 | 4.3 |

The monomers are appropriately solubilized in either DMF or N-methylpyrrolidinone.

Example 6

Synthesis of Peptide Library

A library of 8 mer peptides is synthesized utilizing the protocol of Example 3. The complexity of the library is based upon the 8 amino acids, alanine (A), arginine (R), glycine (G), leucine (L), lysine (K), serine (S), tyrosine (Y) and histidine (H). The monomer are used at 0.3M concentration. FMOC protection is utilized. The monomers and HATU are purchased from Millipore Corp., Bedford, Mass. The membrane is a polypropylene coated with polyhydroxypropylacrylate as described in poster #T81 and accompanying poster #T80 of the 1989 Protein Society meeting, San Diego, Calif. Standard peptide oligomerization protocol are followed.

Example 7

Synthesis of Phosphate Oligonucleotide Library

A library of 10 mer oligonucleotides is synthesized utilizing the protocol of Example 1 with iodine as the oxidizer. The membrane used is a "Nucleic Acid Membrane Support", (from Millipore Corp.—a polyvinylidene difluoride polymeric membrane derivitized with diamine propane). Monomer are standard deoxyribonucleotides purchased from Millipore, Corp., Bedford, Mass. or Glen Research, Sterling, Va.

Example 8

Synthesis of Phosphorothioate Oligonucleotide Library

A library of 10 mer oligonucleotides is synthesized utilizing the protocol of Example 1 with Beaucage reagent as the oxidizer. The membrane used is a "Nucleic Acid Membrane Support", (from Millipore Corp.—a polyvinylidene difluoride polymeric membrane derivatized with diamine propane). Monomer are standard deoxyribonucleotides purchased from Millipore, Corp., Bedford, Mass. or Glen Research, Sterling, Va.

Example 9

Synthesis of Oligoribonucleotide Library

A library of 6 mer oligoribonucleotides is synthesized utilizing the protocol of Example 1 with iodine as the oxidizer. The membrane used is a "Nucleic Acid Membrane Support", (from Millipore Corp.—a polyvinylidene difluoride polymeric membrane derivatized with diamine propane). Monomer are standard deoxyribonucleotides available from either Millipore, Corp., Bedford, Mass. or Glen Research, Sterling, Va.

Example 10

Synthesis of Chimeric Phosphate Oligoribonucleotide-Phosphorothioate Oligodeoxyribonucleotide Library A library of 8 mer oligonucleotides having an internal section of 4 consecutive phosphorothioate deoxyribonucleotides flanked by 2 mer ribonucleotides is synthesized utilizing the protocol of Example 1 with either iodine or Beaucage reagent used as the oxidizer as appropriate. The ribonucleotides are selected as 2'-O-methylribonucleotides. The nucleobases are A, C, G and T for the deoxy portion of the chimera and A, C, G and U for the ribo portions. The membrane used is a "Nucleic Acid Membrane Support", (from Millipore Corp.—a polyvinylidene difluoride polymeric membrane derivatized with diamine propane). Monomers are standard deoxyribonucleotides or 2'-O-methyl ribonucleotides available for either Millipore, Corp., Bedford, Mass. or Glen Research, Sterling, Va.

Example 11

Synthesis of Oligomeric Library Incorporating Propane-1,2-diol Monomeric Units Connected Via Phosphate Linkers A library of 8 mer oligomers based on a propane-1,2-diol backbone linked via phosphate linkages and that incorporates 4 nucleobase for diversity is synthesized utilizing the protocol of Example 1 with iodine as the oxidizer. The membrane used is a "Nucleic Acid Membrane Support", (from Millipore Corp.—a polyvinylidene difluoride polymeric membrane derivatized with diamine propane). Monomer are 1{{N-{2-[9-(N2-isobutyroyl)guanine]-acetyl}amino}}-3-O-dimethyoxytritylmethyl-1-amino-2-O-[(N,N-disiopropylamino)-2-cyanoethoxyphosphite] propane, 1{{N-{2-[9-(N6-benzoly)adenine]acetyl}amino}}-3-O-dimethyoxytritylmethyl-1-amino-2-O-[(N,N-disiopropylamino)-2-cyanoethoxyphosphite] propane, 1{{N-{2-[9-(N4-benzoly)cytosine]acetyl}amino}}-3-O-dimethyoxytritylmethyl-1-amino-2-O-[(N,N-disiopropylamino)-2-cyanoethoxyphosphite]-propane and 1{N-{2-[1-thymidine)acetyl [amino}-3-O-dimethyoxytritylmethyl-1-amino-2-O-[(N,N-disiopropylamino)-2-cyanoethoxyphosphite]-propane.

Example 12

Synthesis of Oligomeric Library Incorporating 3-Hydroxypyrrolidine Monomeric Units Connected Via Phosphate Linkers A library of 6 mer oligomers base on a hydroxypyrrolidine backbone linked via phosphate linkages and that incorporates 6 diversity moieties having various characteristics is synthesized utilizing the protocol of Example 1 with iodine as the oxidizer. The membrane used is a "Nucleic Acid Membrane Support", (from Millipore Corp.—a polyvinylidene difluoride polymeric membrane derivatized with diamine propane). Monomer are $N^1$-palmitoyl-5-dimethoxytrityloxymethylpyrrolidine-3-O-[(N,N-diisopropylamino)-2-cyanoethoxyphosphite, $N^1$-phenylacetyl-5-dimethoxytrityloxymethylpyrrolidine-3-O-[(N,N-diisopropylamino)-2-cyanoethoxyphosphite, $N^1$-(fluorenylmethylsuccinoyl)-5-dimethoxytrityloxymethylpyrrolidine-3-O-[(N,N-diisopropylamino)-2-cyanoethoxyphosphite, $N^1$-(N-Fmoc-3-aminopropionoyl)-5-dimethoxytrityloxymethylpyrrolidine-3-O-[(N,N-diisopropylamino)-2-cyanoethoxyphosphite and $N^1$-(N-imidazolyl)-5-dimethoxytrityloxymethylpyrrolidine-3-O-[(N,N-diisopropylamino)-2-cyanoethoxyphosphite to give a six fold diversity incorporated in the oligomers.

Example 13

Synthesis of Oligonucleoside Library Incorporating Nucleoside Monomeric Units Connected Via Hydroxylamine Linkages A library of 6 mer oligonucleosides linked via methylenehydroxylamino linkages and that incorporates 4 nucleobases as diversity moieties is synthesized utilizing the protocol of Example 4. The membrane used is a "Nucleic Acid Membrane Support", (from Millipore Corp.—a polyvinylidene difluoride polymeric membrane derivatized with diamine propane). Monomers are N4-benozyl-3'-deoxy-3'-

C-formyl-5'-O-phthalimido-5-methylcytosine, N6-benozyl-3'-deoxy-3'-C-formyl-5'-O-phthalimido-adenosine, N2-isobutryl-3'-deoxy-3'-C-formyl-5'-O-phthalimido-guanosine and 3'-deoxy-3'-C-formyl-5'-O-phthalimido-thymidine.

What is claimed is:

1. A chemical reaction apparatus comprising
   a. shaped body having first and second surfaces;
   b. said body having an array of reaction wells therein in fluid communication with each of said first and second surfaces;
   c. porous reaction support in said reaction wells, the porous reaction support comprising fibers having a substantially common axis nornal to the first surface; and
   d. a collection plate adjacent the second surface of the shaped body, said collection plate having a plurality of collection wells in a cooperative array with the array of said reaction wells.

2. A chemical reaction assembly comprising a reaction support having first and second surfaces and being capable of transporting fluid contacting the first surface to the second surface of the support in a direction substantially normal to the first surface, the support being porous and comprising fibers having a substantially common axis normal to the first surface, and a collection plate adjacent to the second surface having a plurality of wells for receiving fluid transported through said support.

* * * * *